(12) United States Patent
Kieken et al.

(10) Patent No.: US 6,763,309 B2
(45) Date of Patent: Jul. 13, 2004

(54) METHOD AND SYSTEM FOR THE DEVELOPMENT OF MATERIALS

(75) Inventors: Laurent Kieken, Menlo Park, CA (US); Enrique Iglesia, Moraga, CA (US); Matthew Neurock, Charlottesville, VA (US); John Matthew Trenkle, Berkeley, CA (US)

(73) Assignee: NovoDynamics, Inc., Ann Arbor, MI (US)

( * ) Notice: Subject to any disclaimer, the term of this patent is extended or adjusted under 35 U.S.C. 154(b) by 94 days.

(21) Appl. No.: 10/068,244

(22) Filed: Feb. 5, 2002

(65) Prior Publication Data

US 2003/0078740 A1 Apr. 24, 2003

Related U.S. Application Data

(63) Continuation-in-part of application No. 09/921,929, filed on Aug. 6, 2001.

(51) Int. Cl.[7] ............................................. G01N 31/00
(52) U.S. Cl. ........................... 702/22; 702/30; 702/81; 702/182; 436/37; 436/147; 436/159; 700/266; 700/268
(58) Field of Search .................. 702/22–24, 30–32, 702/81–84, 19, 27, 79, 181, 183, FOR 115–119, 121, 134, 139, 170; 436/37, 85, 147, 148, 159; 422/197, 198, 196; 502/6, 12, 100, 34, 35, 104, 514, 527.25; 700/266, 268; 435/DIG. 22, DIG. 29, DIG. 30

(56) References Cited

U.S. PATENT DOCUMENTS

| | | | |
|---|---|---|---|
| 5,625,579 A | * 4/1997 | Hinsberg, III et al. | ...... 364/578 |
| 5,774,381 A | 6/1998 | Addis | |
| 6,306,658 B1 | * 10/2001 | Turner et al. | .................. 436/37 |
| 6,373,570 B1 | * 4/2002 | McFarland et al. | ......... 356/364 |
| 6,489,168 B1 | 12/2002 | Wang et al. | |
| 2002/0098471 A1 | * 7/2002 | Weinberg et al. | .............. 435/4 |
| 2003/0077653 A1 | * 4/2003 | Baig | .......................... 435/7.1 |

FOREIGN PATENT DOCUMENTS

EP     1 089 205 A2     4/2001

OTHER PUBLICATIONS

U.S. patent application Ser. No. 60/223,650 B1, Iglesia.
U.S. patent application Ser. No. 09/921,929 B1, Iglesia.
Smith, et al.: "Kinetic Modelling of Higher Alcohol Synthesis over Alkali–Promoted Cu/ZnO and MoS2 Catalysts" chemical Engineering Science, vol. 45, No. 8, 1990, pp. 2639–2646 (Abstract).
Kito, et al.: "An Expert Systems Approach to Computer–Aided Design of Multi–Component Catalysts" Chemical Engineering Science, vol. 45, No. 8, 1990, pp. 2661–2667 (whole Document).
Trimm, David L.: "Chemical Engineering Monographs" (S.W. Churchill (Ed.)) vol. 11: Design of Industrial Catalysts, Elsevier, Amsterdam, NL 1980, p. 3, p. 36.
Happel, et al.: "Multiple Reaction Mechanisms in Catalysis" Industrial and Engineering Chemistry Fundamentals, American Chemical Society, Washington, US, vol. 21, No. 1, (Feb. 1982), pp. 67–76, (Whole Document, especially Paragraph 7 (Conclusions).

* cited by examiner

*Primary Examiner*—Marc S. Hoff
*Assistant Examiner*—Elias Desta
(74) *Attorney, Agent, or Firm*—Pepper Hamilton LLP

(57) ABSTRACT

A catalyst development engine (CDE) provides a rapid approach to the rational development of scalable heterogeneous catalysts and of high-performance solid materials. The CDE includes three main components: the testing cycle, the knowledge cycle, and the knowledge repository or database. The knowledge cycle generates working hypotheses relating performance to key catalyst properties via machine learning methods, computation chemistry and micro-kinetic modeling. Such an approach accelerates development and scale-up of new materials without the impediments introduced by conventional combinatorial approaches based on randomly selected materials.

18 Claims, 19 Drawing Sheets

Inlet NO Conc. = 1760ppm

Reaction is first order in NO

| X1 | X2 | X3 | X4 | X5 | X6 | X7 | X8 | X9 | X10 | X11 | X12 | X13 | X14 | X15 | X16 | X17 | X18 | X19 | X20 | Y1 | Y2 |
|---|---|---|---|---|---|---|---|---|---|---|---|---|---|---|---|---|---|---|---|---|---|
| 12 | MgO | IIA | 2800 | 38 | 35 | 1204.5 | 1.72 | 1.36 | 13.10 | 1.31 | 7.646 | 0.2260 | 1.560 | 10.60 | 1.735 | 1.755 | 1.662 | 0.110 | cubic | 26.24 | 37 |
| 13 | Al₂O₃ | IIIA | 2046.7 | 45 | 43 | 1117.0 | 1.82 | 1.18 | 16.50 | 1.61 | 5.986 | 0.3770 | 2.370 | 6.80 | 1.643 | 3.678 | 1.191 | 0.137 | hexagonal | 24.90 | 38 |
| 20 | CaO | IIA | 2587 | 30 | 43 | 1271.0 | 2.23 | 1.74 | 40.00 | 1.00 | 6.113 | 0.2980 | 2.000 | 22.80 | 1.837 | 2.886 | 2.416 | 0.088 | cubic | 27.01 | 28 |
| 21 | Sc₂O₃ | IIIB | 2405 | 43 | 34 | 1147.2 | 2.09 | 1.44 | 315.00 | 1.36 | 6.540 | 0.0177 | 0.158 | 17.80 | 1.99 | 7.020 | 2.149 | 0.064 | cubic | 29.17 | 28 |
| 22 | TiO₂ | IVB | 1855 | 35 | 46 | 941.6 | 2.00 | 1.32 | 153.00 | 1.54 | 6.820 | 0.0234 | 0.219 | 14.60 | 2.616 | 4.931 | | 0.021 | Rutile | 25.86 | 31 |
| 24 | Cr₂O₃ | VIB | 2300 | 38 | 39 | 753.6 | 1.85 | 1.18 | 180.00 | 1.66 | 6.766 | 0.0774 | 0.937 | 11.60 | 2.5 | 7.352 | 2.251 | 0.026 | hexagonal | 24.16 | 19 |
| 26 | Fe₂O₃ | VIII | 1562 | 27 | 40 | 548.5 | 1.72 | 1.17 | | 1.83 | 7.870 | 0.0993 | 0.802 | 8.40 | 2.95 | 8.685 | 2.695 | 0.013 | hexagonal | 25.31 | 23 |
| 28 | NiO | VIII | 1957 | 45 | 22 | 489.0 | 1.62 | 1.15 | | 1.91 | 7.635 | 0.1430 | 0.907 | 6.80 | 2.37 | 8.407 | | 0.032 | cubic | 29.12 | 16 |
| 29 | CuO | IB | 1336 | 22 | 39.5 | 310.7 | 1.57 | 1.17 | -5.46 | 1.90 | 7.726 | 0.5960 | 4.010 | 6.10 | 2.84 | 3.455 | | 0.015 | | 28.91 | 30 |
| 30 | ZnO | IIB | 1975 | 36 | 24 | 696.7 | 1.53 | 1.25 | -11.40 | 1.65 | 9.394 | 0.1660 | 1.160 | 7.10 | 2.004 | 2.882 | 2.382 | 0.062 | hexagonal | 25.38 | 41 |
| 31 | Ga₂O₃ | IIIA | 1740 | 40.5 | 42 | 720.1 | 1.81 | 1.26 | -21.60 | 1.81 | 5.999 | 0.0678 | 0.406 | 8.12 | 1.935 | 5.506 | | 0.071 | hexagonal | 24.93 | 29 |
| 38 | SrO | IIA | 2430 | 15 | 23 | 1282.8 | 2.45 | 1.91 | 92.00 | 0.95 | 5.695 | 0.0762 | 0.353 | 27.60 | 1.87 | 3.966 | 3.106 | 0.082 | cubic | 31.37 | 15 |
| 39 | Y₂O₃ | IIIB | 2376 | 18.5 | 27.5 | 1172.3 | 2.27 | 1.62 | 187.70 | 1.22 | 6.380 | 0.0166 | 0.172 | 22.70 | 1.91 | 8.662 | 2.521 | 0.075 | cubic | 28.14 | 24 |
| 45 | Rh₂O₃ | VIII | 1115 | 10 | 34 | 190.6 | 1.83 | 1.25 | 111.00 | 2.28 | 7.460 | 0.2110 | 1.500 | 8.60 | | | | | rhombic | 29.81 | 14 |
| 50 | SnO₂ | IVA | 1625 | 27 | 32 | 581.1 | 1.72 | 1.41 | -37.00 | 1.96 | 7.344 | 0.0917 | 0.666 | 7.70 | 1.997 | 4.284 | | 0.063 | tetragonal | 25.89 | 19 |
| 57 | La₂O₃ | IIIB | 2300 | 11 | 20 | 1199.3 | 2.74 | 1.69 | 95.90 | 1.10 | 5.580 | 0.0126 | 0.135 | 31.10 | | | | | hexagonal | 28.54 | 16 |
| 58 | CeO₂ | LANT | 2397 | 26 | 26 | 1089.3 | 2.70 | 1.65 | 2500.00 | 1.12 | 5.540 | 0.0115 | 0.114 | 29.60 | | | | | cubic | 27.75 | 18 |
| 60 | Nd₂O₃ | LANT | 2315 | 12 | 28 | 1206.2 | 2.64 | 1.64 | 5930.00 | 1.14 | 5.530 | 0.0157 | 0.165 | 31.40 | | | | | | 28.67 | 25 |
| 62 | Sm₂O₃ | LANT | 2320 | 19 | 23 | 1211.1 | 2.59 | 1.62 | 1860.00 | 1.17 | 5.640 | 0.0096 | 0.133 | 30.10 | 2.100 | 9.927 | | 0.051 | | 28.42 | 14 |
| 63 | Eu₂O₃ | LANT | 2330 | 16 | 27.5 | 1156.4 | 2.56 | 1.85 | 30900.00 | 1.20 | 5.670 | 0.0112 | 0.139 | 28.80 | 2.105 | 10.047 | | 0.051 | cubic | 27.84 | 23 |
| 64 | Gd₂O₃ | LANT | 2395 | 12 | 26.5 | 1211.2 | 2.54 | 1.61 | 186000.00 | 1.20 | 6.150 | 0.0074 | 0.106 | 27.70 | 2.083 | 10.265 | | 0.052 | cubic | 27.24 | 19 |
| 66 | Dy₂O₃ | LANT | 2385 | 18 | 36 | 1244.4 | 2.49 | 1.59 | 98000.00 | 1.22 | 5.940 | 0.0108 | 0.107 | 24.50 | 2.041 | 10.236 | | 0.058 | cubic | 28.62 | 25 |
| 67 | Ho₂O₃ | LANT | 2395 | 37 | 40 | 1253.8 | 2.47 | 1.58 | 72900.00 | 1.23 | 6.018 | 0.0124 | 0.162 | 23.60 | 1.960 | | | 0.068 | cubic | 29.55 | 32.5 |
| 68 | Er₂O₃ | LANT | 2400 | 36 | 39.5 | 1265.3 | 2.45 | 1.57 | 48000.00 | 1.24 | 6.101 | 0.0117 | 0.143 | 22.70 | 1.950 | | | 0.069 | cubic | 26.43 | 28 |
| 69 | Tm₂O₃ | LANT | 2425 | 34 | 32 | 1259.4 | 2.42 | 1.56 | 24700.00 | 1.25 | 6.184 | 0.0150 | 0.168 | 21.80 | 1.950 | 27.611 | | 0.069 | cubic | 27.35 | 28 |
| 70 | Yb₂O₃ | LANT | 2420 | 30 | 32 | 1210.0 | 2.40 | 1.74 | 67.00 | 1.10 | 6.254 | 0.0351 | 0.349 | 21.00 | 1.940 | 8.160 | | 0.071 | cubic | 26.15 | 29 |
| 71 | Lu₂O₃ | LANT | 2467 | 29 | 35 | 1252.1 | 2.25 | 1.56 | | 1.27 | 5.430 | 0.0185 | 0.164 | 21.90 | 1.930 | 7.962 | | 0.072 | cubic | 27.81 | 26 |
| 72 | HfO₂ | IVB | 2790 | 30 | 30 | 1113.7 | 2.16 | 1.44 | 75.00 | 1.30 | 6.660 | 0.0312 | 0.230 | 16.20 | 2.000 | 4.164 | | 0.063 | monoclinic | 26.79 | 18 |
| 77 | IrO₂ | VIII | 1100 | 24 | 30.5 | 184.1 | 1.87 | 1.27 | 25.60 | 2.20 | 9.100 | 0.1970 | 1.470 | 7.60 | | | | | tetragonal | 32.01 | 16 |
| 90 | ThO₂ | ACTI | 3300 | 22 | 30 | 1227.6 | | 1.65 | 132.00 | 1.30 | 6.080 | 0.0553 | 0.540 | 32.10 | 2.200 | 5.870 | | 0.043 | cubic | 26.51 | 14 |

FIG. 6

METHOD AND SYSTEM FOR THE DEVELOPMENT OF MATERIALS

PRIORITY

This application claims priority to, and is a continuation-in-part of, the U.S. patent application entitled A Knowledge-Based Process for the Development of Materials, filed Aug. 6, 2001, having a Ser. No. 09/921,929, the complete disclosure and drawings of which are hereby incorporated by reference.

FIELD OF THE INVENTION

The present invention relates generally to materials development methods, and, more particularly to a process for the rational development of materials used in chemical processes, including but not limited to heterogeneous catalysts. When applied to heterogeneous catalysts, this process may be referred to as a catalyst development engine (CDE).

BACKGROUND OF THE INVENTION

The still emerging, recent application of combinatorial chemistry to high-speed high throughput synthesis and screening of materials does not adequately address the commercial requirements that a catalyst must meet. Current combinatorial methods are based on random screening of large libraries of materials, prepared and evaluated under unrealistic conditions that are difficult to scale up. Thus, little useful knowledge is derived from such experiments to guide the selection of the next set of experiments or materials and to scale up the material. A different approach for catalytic material discovery and development is needed in order to reduce the time to market which includes scalable high-throughput methods for catalyst synthesis and real-world conditions catalyst evaluation to accelerate generation of useful data coupled with a process that maximizes learning from these data and rapidly and efficiently identifies new material candidates. This knowledge driven process uses integrated scientific and empirical modeling tools to complement and mine experimental data in order to build predictive models that the scientist can use to guide material selection. This knowledge process for rational (as opposed to random) material discovery and development is the subject of this invention.

SUMMARY OF THE INVENTION

The present invention comprises a research process, preferably computer-assisted, for use by the scientist to guide the selection of new materials and accelerate the rational development of materials. This system comprises a Knowledge Cycle™ (KC), a Testing Cycle™ (TC) and a knowledge management system. The KC comprises data-based and science-based modeling tools that are integrated in a knowledge management system, in order to maximize learning and enhance the scientist's decision-making capabilities for efficient experiment planning.

Additional advantages of the invention will be set forth in part in the description which follows, and in part will be learned from the description, or may be learned by practice of the invention. The advantages of the invention will be realized and attained by means of the elements and combinations particularly pointed out in the appended claims.

The above and other features and advantages are achieved through the use of a novel material development process as herein disclosed. In accordance with one embodiment of the present invention, a method of identifying chemical reaction mechanisms for a chemical process includes the step of specifying a reactant set that includes a plurality of chemical substances that may engage in a chemical reaction with one or more other substances in the reactant set. It also includes the step of specifying a plurality of possible products that may result from the reaction of two or more of the substances included in the reactant set. It also includes the step of identifying a reaction mechanism set that includes a plurality of reaction mechanisms, wherein each reaction mechanism is a combination of two or more elementary steps representing the chemical process. It also includes the step of selecting a plurality of catalytic materials, where each catalytic material is associated with at least one of the reaction mechanisms in the reaction mechanism set, and each catalytic material is also associated with experimental data. It also includes the steps of associating a kinetic constant value with each elementary step of each reaction mechanism, as well as generating a kinetic model associated with each reaction mechanism and each catalytic material. Further, it includes the step of using a processing device to screen the reaction mechanism set by applying a goodness of fit test to the experimental data associated with each catalyst, eliminating the reaction mechanisms having a worst fit, and grouping the remaining reaction mechanisms associated with each catalytic material to provide a first reaction mechanism subset for each catalytic material.

Optionally, the method also includes the steps of selecting a performance variable and, for the reaction mechanisms contained in the first reaction mechanism subset, identifying one or more associated kinetic parameters to which the performance variable is most sensitive.

The method of may also include the steps of using a processing device to calculate a modeled kinetic constant for a plurality of the elementary steps associated with a plurality of the reaction mechanisms using the processing device to screen the first reaction mechanism subset by eliminating the reaction mechanisms having associated kinetic constants that least closely relate to their corresponding modeled kinetic constants, and associating the remaining reaction mechanisms not eliminated in the second screening step with a second reaction mechanism subset. In this option, the calculating step may comprise using molecular modeling to calculate the modeled kinetic constant. Also, the option may include the additional steps of selecting a performance variable, and, for the reaction mechanisms contained in the second reaction mechanism subset, identifying one or more associated kinetic parameters to which the performance variable is most sensitive.

In accordance with an alternate embodiment of the invention, a method of identifying materials for the performance of a chemical process includes the step of selecting a data set for a set of materials. The data set includes one or more dependent performance variables for a chemical process, as well as independent variables including, but not limited to, calculated or measured properties of the materials or preparation parameters relating to the materials. The method also includes the step of building a model that correlates the dependent performance variables with one or more of the independent variables, as well as the step of identifying one or more of the independent variables having values that yield improved values of the dependent performance variables based on the results of the model built in the building step. Further, the method includes the step of identifying one or more new materials that are associated with the values of the one or more independent variables that yield improved values of the dependent variables.

Optionally, in this embodiment, the step of building a model comprises the use of recursive partitioning. Also optionally, one or more dependent performance variables or one or more independent variables may comprise kinetic parameters that have been associated with reaction mechanisms in a reaction mechanism set. Also optionally, the method may include the steps of applying a Monte Carlo kinetic simulation to calculate at least one modeled performance parameter for each material included in the material set, and selecting at least one materials class based on the results of the Monte Carlo simulation.

Further, the method may include the steps of (i) selecting a selected reaction mechanism from a reaction mechanism set, wherein each reaction mechanism in the set comprises a combination of two or more elementary steps in a chemical process; (ii) applying a Monte Carlo kinetic simulation to calculate at least one modeled performance parameter for each material identified in the identifying step, wherein the simulation is associated with the selected reaction mechanism; and (iii) selecting at least one materials class based on the results of the Monte Carlo simulation. With this option, each reaction mechanism in the reaction mechanism set may have been screened, using a goodness of fit test, to eliminate reaction mechanisms for which experimental data associated with reaction mechanism catalysts has been determined to have a poor fit. Each reaction mechanism in the reaction mechanism set may have been further screened to eliminate reaction mechanisms having associated kinetic catalysts that least closely relate to corresponding modeled kinetic constants.

In accordance with an alternate embodiment, a process for the development of scalable, high-performance materials includes a computer-assisted knowledge cycle that uses at least one of (i) input from existing experimental data; (ii) correlations generated from at least one of experimental, theoretical, and/or modeling findings; and (iii) theoretical and modeling investigations to generate working hypotheses and suggested steps for at least one of experimental investigations and theoretical investigations to guide the search for better materials.

Optionally, the knowledge cycle further may also include the use of kinetic modeling to guide catalyst development. The knowledge cycle may also include the use of machine learning methods to guide catalyst development, as well as using kinetic Monte-Carlo simulation to screen catalytic surfaces for catalytic performance.

There have thus been outlined the more important features of the invention in order that the detailed description that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be used as a basis for designing other structures, methods, and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The accompanying drawings, which are incorporated in and constitute a part of this specification, illustrate one embodiment of the invention and together with the description, serve to explain the principles of the invention. In the drawings:

FIG. 6 illustrates exemplary data for the identification of key catalyst properties.

DETAILED DESCRIPTION OF THE PREFERRED EMBODIMENTS

The present invention is a method of discovering, developing, and optimizing materials. The method may be applied to the development of new heterogeneous catalytic systems. Reference will now be made in detail to the present preferred embodiments of the invention, examples of which are illustrated in the accompanying drawings.

Figure 1:
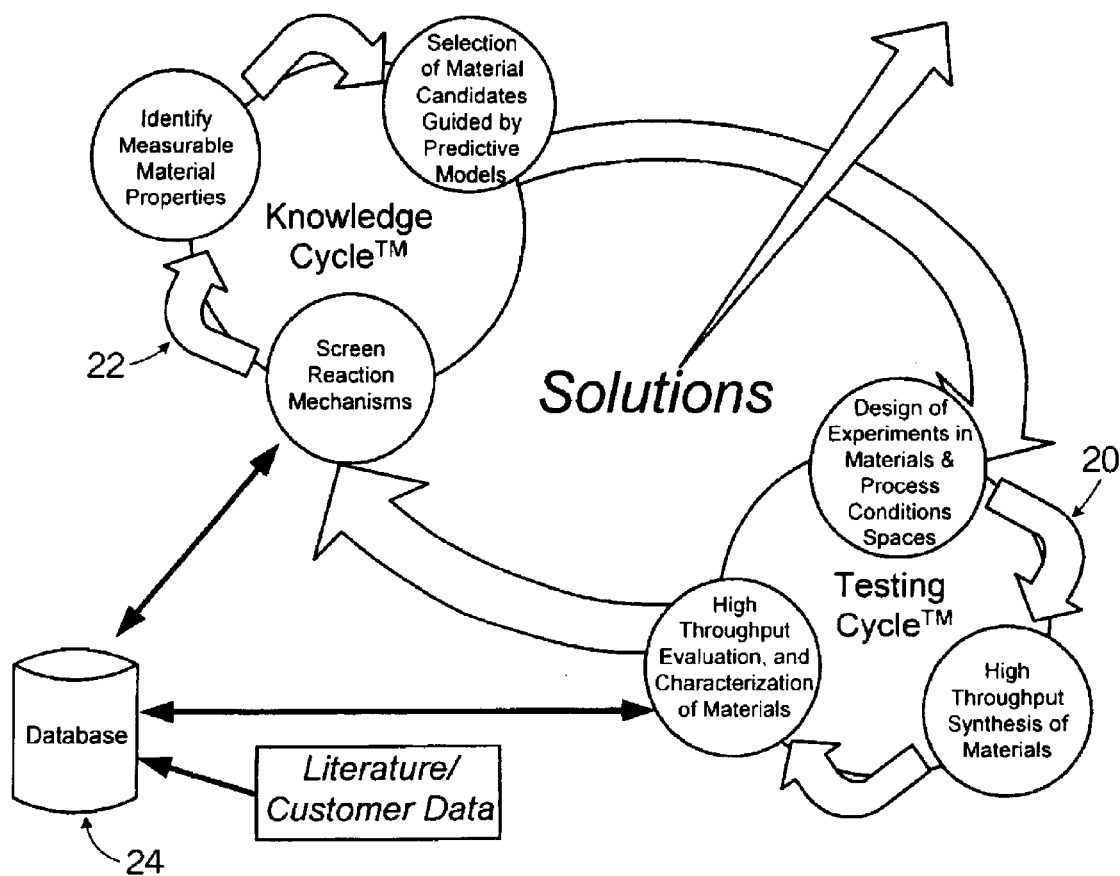
FIG. 1 is a schematic diagram showing a preferred embodiment of the catalyst development engine.

This section provides an overview of the catalyst development engine (CDE) of the present invention and discusses the tools and methods required for data analysis and mining, predictive model development and catalytic materials selection. The topics discussed under this heading are the key components of the novel CDE depicted in FIG. 1. The engine provides a rapid approach to the rational development of scalable heterogeneous catalysts and high-performance solid materials. The CDE includes three main components that are intimately connected in an integration framework: (1) a testing cycle (TC) 20 for experimental data generation; (2) a knowledge cycle (KC) 22 for data analysis and subsequent experiment planning; and (3) a knowledge repository 24 (e.g., a database).

The primary function of the TC 20 is to rapidly generate informative data for the experimental evaluation of new catalytic materials and also generate data on well-characterized systems and for probe reactions of materials properties such as, but not restricted to, acidity, basicity, reducibility, etc. for use in the KC 22. The primary functions of the KC 22 are (1) to generate working hypotheses relating performance to key catalyst properties that will guide the search for even better catalysts and (2) to generate fundamental structure-property relationships that will be instrumental in the selection of catalysts for further experimental evaluation in the TC 20. Both cycles run concurrently and feature theoretical and experimental activities that are highly integrated. The knowledge repository expands after each iteration of the CDE. The knowledge repository inventories materials properties and catalyst performance data for a comprehensive database of materials and for characteristic probe reactions of materials properties. It contains both experimental and theoretical data. Such an approach accelerates development and scale-up of new materials without the impediments introduced by conventional combinatorial approaches based on randomly selected materials. Preferred components and activities of the CDE are described in more detail in the following table (Table 1), and illustrated in FIG. 2.

TABLE 1

Catalyst Development Engine—Research Process Description

| | |
|---|---|
| | Statement of Problem: Entails a concise statement clearly defining project goal(s) in terms that can be reasonably and adequately addressed with the tools available. |
| Prior Data | All pertinent available data, independent of source, are collected, evaluated and stored in the knowledge repository in a format that is usable in the CDE. |
| | Testing Cycle: In this cycle, the emphasis is on a rapid selection, preparation, and evaluation of potential catalysts. |
| Catalyst & Test Selection | The catalyst target is selected for evaluation, which includes determining what performance tests are meaningful, e.g. rate, selectivities, conversions, heats of adsorption, etc. |
| Experimental Design | The selected catalysts are prepared and evaluated according to an experimental design matrix. This ensures that the significant variables are effectively examined with the minimum number of experiments, while maximizing the information gathered. |

TABLE 1-continued

Catalyst Development Engine—Research Process Description

| | |
|---|---|
| Synthesis, and Evaluation | The catalysts are prepared using validated methodologies and HTP tools. They are synthesized and evaluated for key properties and performance as prescribed by the experimental design. |
| | Knowledge Cycle: This cycle uses literature, Testing Cycle data, theoretical chemistry and simulation data to (1) Discriminate between reaction mechanisms; (2) Identify key measurable catalyst properties via molecular or empirical modeling; and (3) Derive structure-property models to guide catalyst search. |
| Screen Reaction Mechanisms | Microkinetic modeling is applied to identify critical mechanistic steps that limit performance and associated kinetic parameters. Its functions include: Generate mechanisms based on reactant, product, and possible intermediates Discriminate between reaction mechanisms based on goodness of fit with experimental data and with realistic constraints on kinetic parameters based on measurements or molecular modeling calculations. Perform sensitivity analysis on kinetic parameters to identify important ones. Mechanisms that can reproduce general trends in existing data are studied in more detail with molecular modeling to further evaluate their validity. |
| Identify Key Catalyst Properties | Experimental theoretical and simulation data are modeled with empirical machine learning algorithms to generate hypotheses relating catalyst descriptors including properties (e.g. binding energies, activation energies, other surface properties) and synthetic parameters to key kinetic parameters or to performance |
| Guide Selection of Material Candidates for Subsequent Experiments | Electronic structure, composition/structure, particle size, support, and promoters can affect the surface properties of catalysts. Developing trends that relate catalyst descriptors to these properties will assist the scientist in deciding what "knob" to turn in order to tune the catalyst properties. Screen virtual surfaces for performance using Monte-Carlo simulation using semi-empirical and ab initio computational methods for kinetic parameter estimation. Develop guiding trends across materials classes. Develop optimal lead catalytic systems using predictive machine learning methods such as recursive partitioning, neural networks or genetic algorithm to estimate performance of new materials from catalyst descriptors |
| | Iterations: Using the knowledge gained from the current cycle a determination is made on how to proceed; either by preparing another round of targets or by terminating this phase of the project because the catalyst meets the project goals or it is a dead end and the project continuation is evaluated. |
| | Solution to Problem: When a new catalyst that meets the performance criteria is identified, it is considered for scale-up and commercial development |

The process outlined in Table 1 is a novel decision-support tool for the researcher to use interactively in the development of new catalytic materials. The CDE integrates various modeling tools—computational chemistry tools, kinetic modeling, and machine learning—with a knowledge management system to house the significant experimental and theoretical knowledge for its efficient future use in the guided development of new catalytic materials.

Figure 3A:
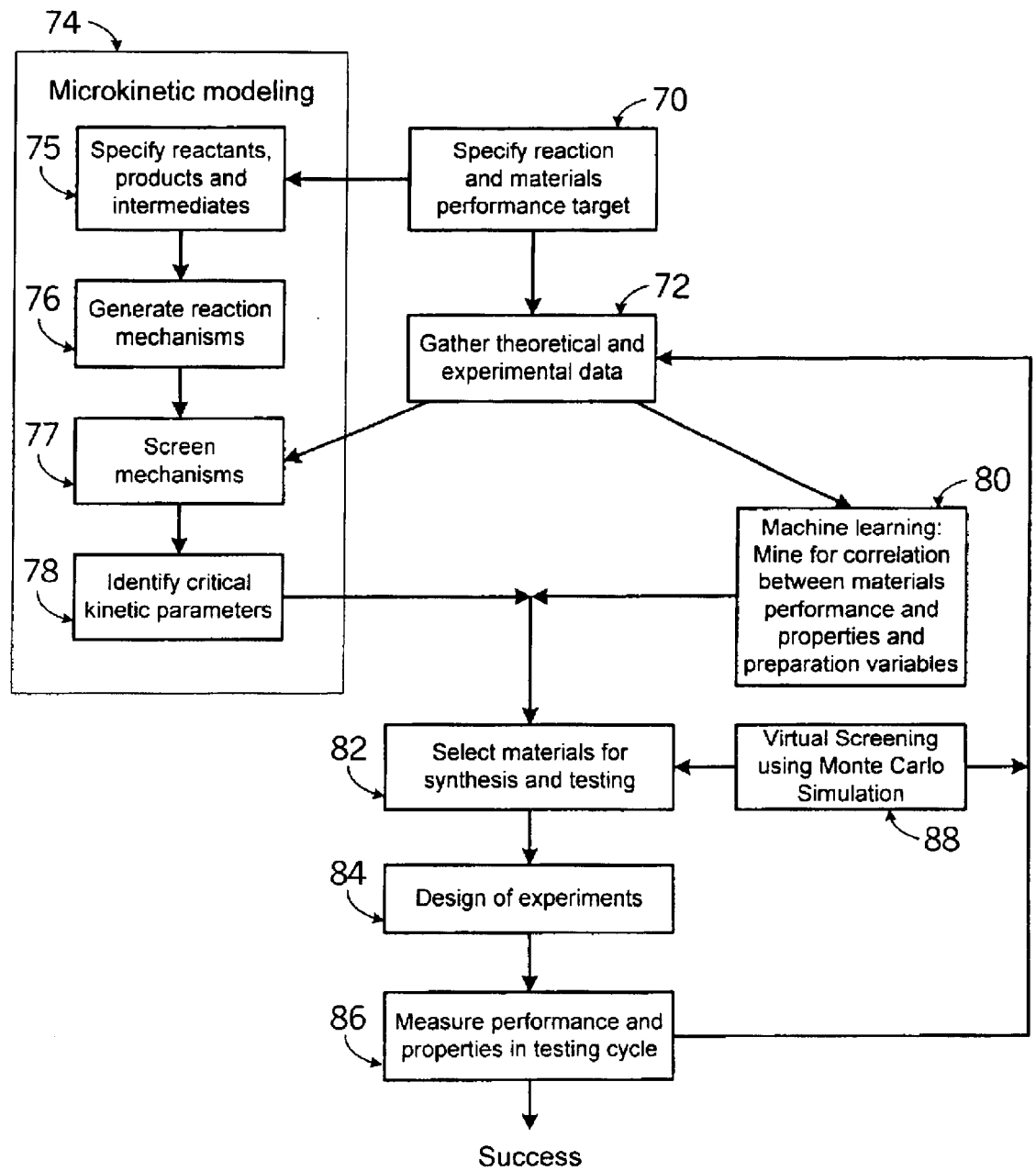
FIGS. 3a and 3b illustrate exemplary and optional steps included in preferred embodiments of a knowledge cycle.
Figure 3B:
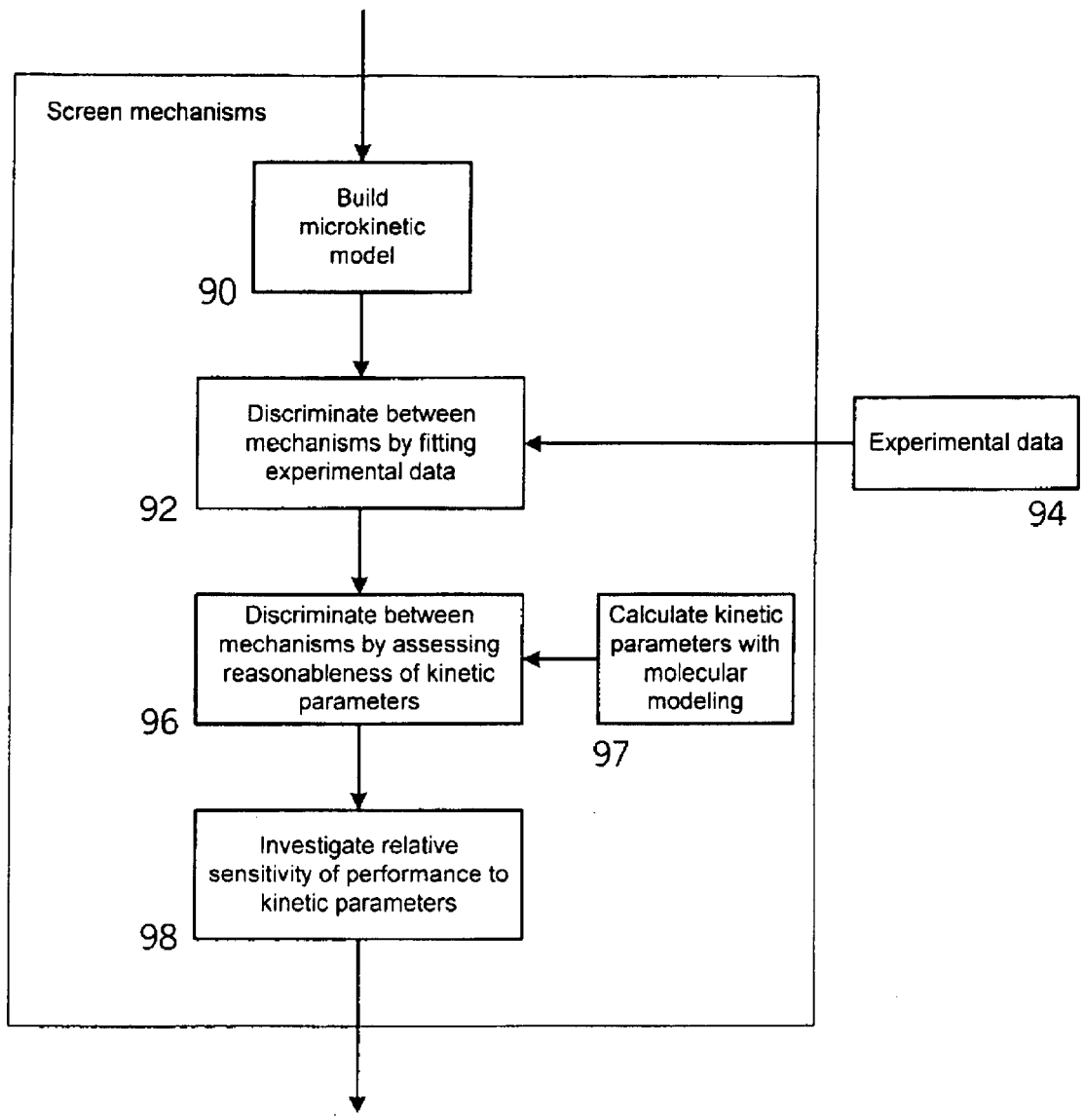

FIGS. 3a and 3b provide additional detail about the knowledge cycle element of the present invention. Referring to FIG. 3a, the performance target or targets and desired reaction(s) are identified (step 70). Theoretical and experimental data are also gathered (step 72), from existing sources, from new research, and/or from the knowledge cycle process itself. The knowledge cycle can use either a microkinetic modeling approach (step 74) or a machine learning approach (step 80). Optionally, a combination of the two approaches may be used.

With the microkinetic modeling option (step 74), the cycle includes the specification of reactants, products, and intermediates (step 75), the generation of reaction mechanisms (step 76), the screening of mechanisms (step 77), and the identification of critical kinetic parameters (step 78). The screening step (step 77) is further illustrated in FIG. 3b. Referring to FIG. 3b, based on a microkinetic model 90 and experimental data 92, a goodness of fit test is performed (step 92) between the experimental data and the data generated by the model to eliminate the reaction mechanisms for which the fit is not good. A second cut is taken by using kinetic parameters calculated with molecular modeling (step 97), and assessing the reasonableness of kinetic parameters associated with the mechanisms (step 96). The relative sensitivity of the catalyst performance to the various kinetic parameters is also assessed (step 98), with a preference expressed for the parameters having the highest levels of sensitivity.

Returning to FIG. 3a, in addition to the microkinetic modeling, databases of information gathered can be mined using one or more of many types of machine learning and pattern recognition techniques to identify correlations between performance, properties, and preparation variables (step 80). These correlations become the basis for the selection of materials. These potential materials can be screened further using Monte Carlo kinetic simulation (step 88). In this step, catalytic performance of a virtual catalyst candidate can be calculated. Using one or a combination of these options, materials are selected for synthesis and testing (step 82), experiments are designed (step 84), and performance and properties are measured in a testing cycle (step 86).

The following sections describe, in additional detail, the modeling tools that are suitable for treating heterogeneous catalyst problems: the computational chemistry methods, the microkinetic and Monte-Carlo modeling techniques for performance prediction, and the machine learning algorithms that together make the CDE™ approach novel and viable.

Computational (Modeling) Methods

Current state-of-the-art molecular modeling of catalysts involves either ab initio quantum chemical methods or semi-empirical methods. Ab initio quantum chemical methods are first-principle solutions to the Schrödinger equation, which make only a few very basic approximations. Because of the high level of detail and accuracy, they are applicable to essentially any material system but they require high computational intensity. They provide the best accuracy for a wide range of chemical and catalytic properties. These methods are used to examine the chemisorption and reactivity of all reactants, intermediates, and products at different surface coverages in order confirm the reaction mechanism and provide the parameters necessary for detailed microkinetic models (adsorption energies, activation energies, rate constants). In addition, a large set of chemical and catalytic properties for different catalytic systems are evaluated in order to develop a set of property libraries that are used to establish correlations (metal-adsorbate bond strengths, site acidity, site basicity, oxidation potential, etc.) and hypotheses tests.

Semi-empirical methods include both empirical theoretical models, such as Bond Order Conservation, and semi-empirical quantum chemical methods. Semi-empirical quantum chemical methods attempt to minimize the computational efforts required to solve the Schrödinger equation by approximating multi-center integrals that slow down computation. These approaches range from very approximate calculations such as extended Hückel calculations, which simply ignore the contributions from multi-center integrals, to very approximate methods using low computational times on the order of a few minutes. More sophisticated methods treat the multi-center interaction integrals using empirical information. They typically use experimental data or ab initio results in order to parameterize the integrals.

In terms of ab initio methods, Density Functional Theory (DFT) calculations provide the state-of-the-art for modeling catalytic systems and they can be used to predict chemisorption energies, overall reaction energies, activation barriers, and chemical properties descriptors which target key catalytic properties, such as acidity, basicity, and reducibility. Gradient-corrected DFT methods have proven to be the most robust and accurate methods for the prediction of large transition-metal systems due to their ability to explicitly treat electron-electron correlation. The active surface sites can be approximated by using either a metal cluster model to represent the coordination and bonding of the active metal particles, or a periodic slab model that represents larger exposed surfaces. The accuracy of DFT methods in predicting energetics for transition metal systems is +/−5 kcal/mol. Although quantitative accuracy is important, the ability to predict the relative trends across the periodic table is more critical for the identification of useful catalyst targets. This enables scanning of a range of unknown systems for optimal metal-adsorbate bond strengths and surface reactivity.

These detailed calculations can be used to understand and predict the trends in both chemisorption and surface reactivity across the periodic table. Non-local cluster and periodic slab DFT calculations have been used to compute the binding energies of maleic anhydride on the 111 surfaces of Pd, Re, Au, Pd/Re, Pt, Pd/Mo, and Pd/Au. Basic concepts from frontier molecular orbital theory are subsequently used to construct a general model that is able to predict a priori the outcome of the more detailed ab initio calculations. These models provide an understanding of the controlling factors that govern chemisorption as well as a knowledge-driven approach to the screening of multi-metallic and metal oxide systems by simply computing a particular chemical descriptor (in this case the center of the d-band at the surface layer of the metal). This model is further extended to predict activation barriers for different elementary steps in the overall catalytic path. As such, studies show that the reactivity of the surface scaled with the relative location of the d-band center of the metal with respect to the Fermi level. Also, the reaction kinetics over different (111) surfaces is found to correlate quite well with changes in the center of the d-band. There is an optimal trade-off between different reactions. As the metal-adsorbate bond becomes too weak it becomes difficult to dissociate hydrogen on the surface. This shuts down the overall reaction.

While DFT quantum mechanical method are appropriate for establishing the reaction mechanism, and for accurately calculating properties for a large number of systems, the calculations can still require 1–2 days per simulation. In order to offer daily guidance and be able to lead high-throughput screening efforts, a much faster method needs to be developed. The present invention uses a variety of semi-empirical methods that run for a few minutes to determine specific catalytic properties within reasonable accuracy. These methods, driven by the scientist, can be coupled with advanced machine learning methods, that are described later, in order to develop a potential set of lead catalytic systems which meet the target properties.

Another semi-empirical method is the Atomic Superposition Electron Delocalization Molecular Orbital Theory (ASED-MO). ASED may be used to describe many qualitative features and, in some cases, it can provide quantitative assessments in catalysis. The applicability and accuracy of the approach depends on developing appropriate parameters.

The present invention generates very detailed ab initio libraries as well as empirical databanks, which can be used to parameterize these systems more accurately. By way of simple comparison, we examined how well we can infer trends in binding energies by comparing simple ASED calculation which were optimized to detailed DFT calculations. We found that the results show the correct trends to within 30% for NO, O, and N binding energies over a set of different metals. The application of structural optimization as well as refined regression of the parameters should improve the accuracy to 10–20%.

In addition to refined ASED models, we have developed a more approximate Bond-Order Conservation (BOC) method. While BOC has some ties back to quantum chemical descriptions of bonding, it is a very simple approach that does not attempt to solve the Schrodinger equation. The approach offers some predictions of reactivity. The present inventors have found that some of the known shortcomings of this method can be overcome by determining interaction parameters from first-principle DFT methods. Also, tight binding or single-SCF DFT methods are used and evaluated for the most appropriate compromise between accuracy and speed.

Microkinetic Analysis

Microkinetic modeling incorporates the basic surface chemistry, i.e., elementary steps, in the kinetic description of a catalytic reaction. Such a kinetic model is a very useful tool to compare and extrapolate the performance of different catalytic materials at various process conditions. It is used to eliminate postulated reaction mechanisms that are not consistent with experimental data. Given a plausible mechanism, microkinetic analysis can also identify to the small number of critical kinetic parameters that are required in order to describe the overall rate of the catalytic process. This is accomplished by performing a sensitivity analysis of catalytic performance with respect to all kinetic parameters. Knowledge of the critical kinetic parameters and associated steps can provide the scientist with insights on how to modify materials in order to increase the overall performance.

In the Catalyst Development Cycle, the microkinetic analysis may include one or more of the following steps:

(1) Mechanism enumeration: Given a catalytic reaction, various possible mechanisms are enumerated based on the list of observed products and possible intermediates, list of plausible elementary steps, experimental kinetic data on a training set of materials, literature data, and chemistry rules. For example, steps that require the simultaneous reaction of more than three reacting species or the breaking and forming of too many chemical bonds are usually not elementary and can be excluded. Reaction pathways can also be computer-generated by assuming again that an elementary step involves only a small number of changes in the bonding of the reactants, i.e., three or four changes in the connectivity of the reactants via bond cleavage and formation.

(2) Mechanism discrimination: There is usually a deficit of information for the values of kinetic rate constants of elementary steps, especially for the activation barriers. Good estimates of pre-exponential factors can be obtained from collision rate theory and transition-state theory. Molecular modeling can also be used to constrain the possible value of activation barriers. The remaining unknown kinetic parameters become adjustable parameters that are determined by fitting the kinetic model to experimental data. Experimental design is used to determine the optimal process variable space for kinetic parameter estimation. Discrimination between two mechanisms is accomplished based on how well each mechanism reproduces the experimental kinetic features as process variables are varied. Additional experimental data may be required for discrimination as the optimal process variable space for mechanism discrimination may differ from the one used for kinetic parameter estimation.

(3) Kinetic parameter discrimination: Mechanisms which can no longer be distinguished based on experimental data (because the process variable space for discrimination is not accessible experimentally) can be examined for the reasonableness of their values of the kinetic parameters (4) Sensitivity analysis: A sensitivity analysis of the overall catalytic performance with respect to the kinetic parameters of the elementary steps is carried out on the remaining few reaction mechanisms which have passed steps/filters (2) and (3). The most sensitive parameters are the critical parameters to be altered (5) Relate critical kinetic parameter to material properties: This step is probably the most challenging as kinetic parameters may depend on complex combinations of measurable materials properties. Postulated materials properties may be tested for relevance by synthesizing and testing materials with varying values of that property or by calculating with molecular modeling the critical kinetic parameter and the specific property for a series of model catalytic surfaces. The outcome of that step is one or several structure-property relationships that relate kinetic or thermodynamic parameters to a measurable materials property.

(6) Parameter optimization: Optimum values of the kinetic parameters are calculated from the microkinetic model(s) given the targeted value for the overall catalytic performance. These values are compared to the structure-property relationship in order to assess whether or not a candidate material with the required properties is plausible or not. This information is used to select materials to be investigated in the next iteration of the TC.

The reaction pathway for a catalytic process depends on the properties of the materials, hence experimental kinetic data on new materials from the TC must be re-processed through steps (2) through (6) to investigate possible changes in reaction pathways and to update the kinetic hypothesis and the associated structure-property relationships.

Monte-Carlo Simulation

As in microkinetic analysis, kinetic Monte-Carlo simulation can be used to simulate the rate of elementary surface processes. However, Monte-Carlo simulation takes into account the explicit effects of surface coverage, local surface atomic composition, structure, and spatial arrangement. The effects of surface poisons and promoters on catalytic performance can also be simulated. This technique can, for example, simulate the essential features of the kinetics of the catalytic hydrogenation of ethylene on Pd(100). Other simulations are, of course, possible. The Monte Carlo method successfully describes the relative kinetic trends as process variables are altered and, in some cases where the metal surface structure is well defined, it has captured some degree of quantitative accuracy. This approach is unique in relating overall catalytic performance to surface materials properties. While the Monte-Carlo kinetic simulation has been used to elucidate the effects of local structure on the catalytic process, its application to systematic virtual screening of catalytic surfaces is novel in the CDE. In this invention, it is used to predict the relative performance (activity, selectivity, life—under steady-state and/or transient conditions) of virtual catalytic surfaces as a function of process variables and materials surface properties and to provide relative ranking of these surfaces. Surfaces that show promising catalytic properties can then be explored further experimentally. This tool is aimed at guiding the scientist in the exploration and optimization of catalytic materials.

As in the micro-kinetic analysis the catalytic process must be broken down in a series of elementary steps or lumped elementary steps. The Monte-Carlo algorithm tracks the spatial and temporal changes of all surface intermediates in order to simulate the kinetics. Values for activation barriers and pre-exponential factors for these steps are necessary input to the model. Pre-exponential factors can be taken from the experimental literature if available or calculated from transition-state theory and collision rate theories. Activation barriers can be obtained from experiment, ab initio calculations or semi-empirical methods such as BOC theory. The latter methods, while less accurate than first-principle quantum chemistry calculations, are considerably faster and thus can be used for fast screening of catalytic surfaces and their relative ranking. The bond energies of the atomic species used in BOC theory are calculated from ab initio computational chemistry. Effects of lateral interactions between different species as a function of their distance within the catalytic surface grid are separated into through-surface interactions, where the presence of a neighboring adsorbs species affects the local surface electronic properties, and through-space adsorbate-adsorbate interactions. The former can be quantified using BOC theory and the latter using a molecular mechanics model such as a Force-Field model for example.

The Monte-Carlo algorithm examines all reaction scenarios on a combination of different grid sites (atop, bridge, hollow) and different grid ensembles and then assesses their probability of occurrence and rate based on site proximity and occupancy for the reactant and product states of the reaction. When a reaction scenario is possible, binding energies of reactants, products, and intermediates are calculated at the appropriate surface sites. All possible surface scenarios are computed and stored. The overall rate of each elementary step is then calculated based on the number of possible scenarios. Each step is classified as being either in equilibrium or dynamic based on their rate. In the randomly generated time-event, the dynamic reaction that occurs is chosen based on its relative rate as compared to the sum of the rates of all dynamic processes. All equilibrium processes, including surface diffusion, are allowed to occur after every time.

Validation of the simulated results against experiment for a training set of materials is critical because of the assumptions present in the kinetic parameter estimations.

Machine Learning Techniques

Machine learning is the process of building from a set of data a data structure, i.e. model, from which new insights, knowledge and learning can be derived. Two possible applications of machine learning in the KC of the CDE are (1) the identification and ranking of critical descriptors or combination of descriptors, including chemical properties such as acidity, basicity, and reducibility and also process variables important to the preparation and treatment of materials; and (2) the selection of materials candidates or experimental compositional as well as process parameter regions to be explored experimentally based on the prediction of the learning model. While machine learning techniques have been applied earlier for the development of heterogeneous catalytic materials, their success has been very limited due in part to the small amount of reliable data available and the choice of machine learning methods. The recent development of high-throughput techniques and equipment for the synthesis and assay of catalytic materials is enabling the collection of much larger data sets in a much shorter time and thus is making the application of these data-driven techniques more important and productive in the development of new catalytic materials.

There are a number of machine learning techniques available, which can be categorized into two classes: supervised and unsupervised learning. The selection of a particular technique depends on the question that the scientist is asking. Supervised learning allows for prediction based on the data model that is generated from the training set. Unsupervised learning methods generate the data model itself from the training data. The KC contains a toolbox of machine learning algorithms that can be selected based on the inquiry of the scientist. A representative list of methods is shown in Table 2. Other methods could be used as well.

TABLE 2

Selected Machine Learning Techniques

| | |
|---|---|
| Neural Networks | Decision Trees, especially ensembles of such trees |
| Bayesian Net | Genetic Algorithms/Genetic Programming |
| Simulated Annealing | Tangled Hierarchies of Sets |
| Recursive Partitioning | Clustering |
| Hidden Markov Models | Fuzzy Methods |
| Semantic Networks | Naïve Bayes |
| Similarity Mapping | Support Vector Machines |
| Self-organizing Maps | Gaussian Processes |

Knowledge Management System

Figure 2:
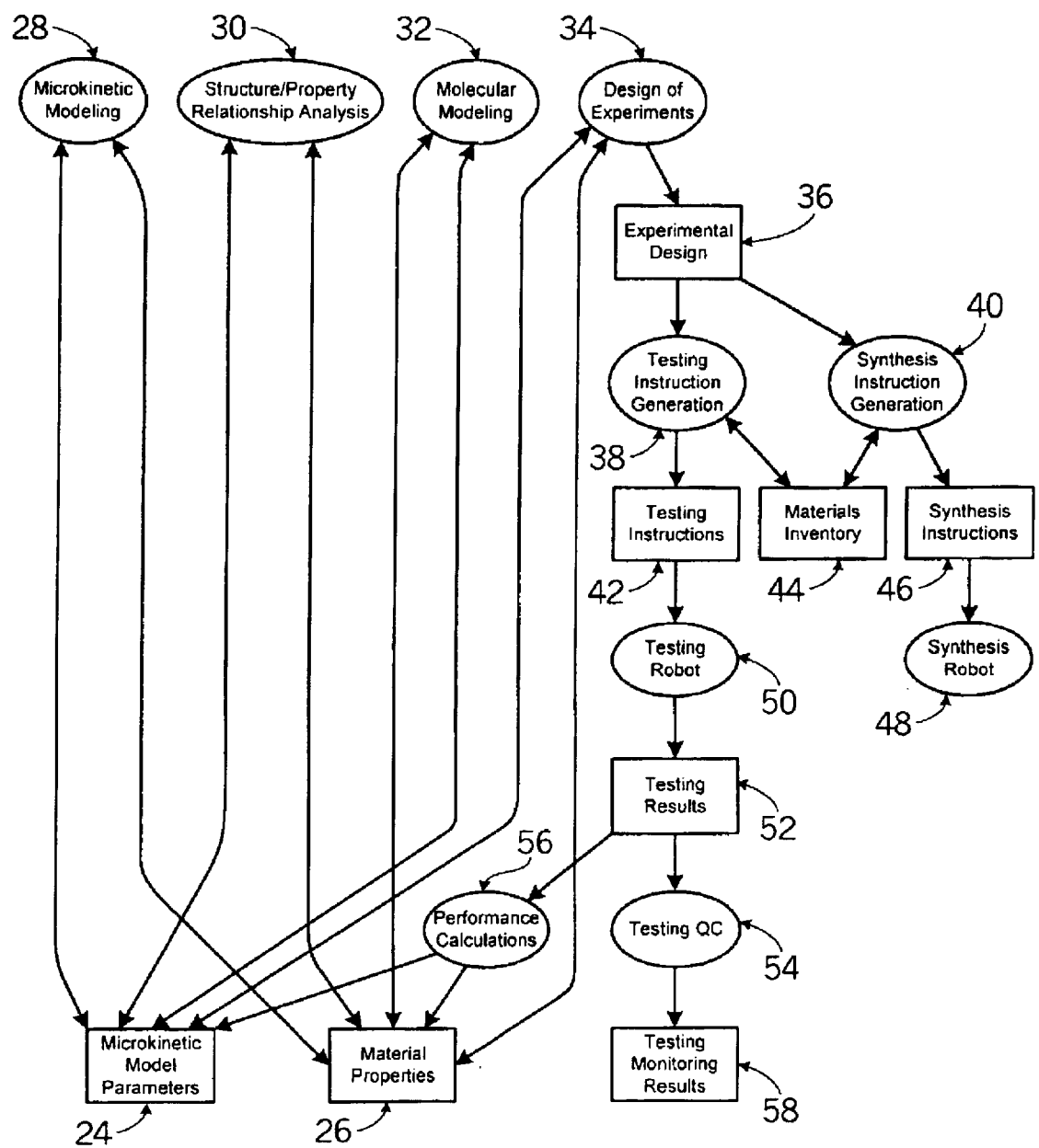
FIG. 2 is a schematic diagram showing the underlying architecture of the catalyst development engine.

A schematic diagram of a preferred embodiment of the CDE is shown in FIG. 2. The CDE is based on valuable catalyst and reaction knowledge and an understanding that is used to solve catalytic problems. Easy access, retrieval, and archival of this knowledge improves the decision-making ability and productivity of the process. The knowledge system is the information retrieval system that integrates multiple information sources and integrates them in a logical fashion. The information sources include experimental data, modeling, and theoretical data, from literature and from proprietary corporate files. For example, information from kinetic modeling and molecular modeling on reaction elementary steps for a particular catalytic reaction is stored so that it can be re-used easily for a different catalytic reaction which shares one or more elementary steps with the previous reaction. This information may be textual, numerical, structural, or logical, and may reside internally or remotely from the database. The knowledge management system preferably includes an interactive interface for use by the researcher in each step of the process.

Description of the Catalyst Development Engine

The role of the KC is to greatly augment the scientist's ability and efficiently in retrieving knowledge that is critical to guiding the catalyst development. These tools aim to maximize learning and guide catalyst selection. Critical tasks are described further below.

(1) Develop an empirical learning model

Composition/structure, particle size, support, and promoters can affect the surface properties of catalysts. Developing trends relating key surface properties to these parameters will assist the scientist in turning the catalyst properties. An analysis of existing experimental and theoretical data with machine learning algorithms such as tree analysis can be used to uncover patterns in the theoretical and experimental data even in highly non-linear systems. Data for important descriptors are mined and correlations between performance and these descriptors are formulated. Descriptors include synthetic parameters as well as experimental and theoretical bulk and surface properties. This information can be used to construct a working hypothesis for the catalytic reaction, which is tested against new data and improved, at each iteration of the CDE cycle.

(2) Construct a microkinetic model to screen reaction mechanisms and identify key kinetic parameters Microkinetic modeling will be used to narrow the list of plausible reaction mechanisms that will be investigated further by molecular modeling. A microkinetic model will be built for various postulated reaction mechanisms. The performance of the materials will be calculated as a function of temperature and reactant and product concentrations for a catalyst training set. Mechanisms that can reproduce the general trends in experimental data will be studied further. Sensitivity analysis will be performed on the rate constants of elementary steps to identify the critical kinetic parameters and how they affect overall performance. These critical parameters will be related to materials properties using data on a series of materials in order to identify trends more easily, and using scientific prior knowledge and know-how.

(3) Construct theoretical models

Computational chemistry will be used to provide understanding of the reaction mechanism and confirm/strengthen/propose hypotheses (relating key catalyst properties to kinetic parameters of elementary steps. NDI will use ab initio DFT periodic slab molecular modeling techniques to examine the elementary surface reaction steps for the reaction. These methods will be used to calculate binding energies, activation barriers, as well as rate constants for elementary steps. Calculated rate constants will be inserted in the microkinetic model. Critical rate constants will be correlated with surface properties in order to identify key material properties. The initial calculations will be done on a catalyst "training" set. The catalyst training set will be synthesized and tested to validate the calculations and identify any limitations of the model. The model will then be refined to account for differences between calculated and observed surface properties and rate constants and to improve the model. As lead catalysts are identified experimentally, the modeling work will focus more specifically on these materials.

(4) Virtual screening to guide catalyst selection

Faster semi-empirical methods (calibrated with ab initio calculations) are used to calculate kinetic parameters and insert them into a kinetic model. Catalytic performance is calculated as a function of surface composition, structure, atomic spatial arrangement using Monte-Carlo simulation. This kinetic model can be coupled with an optimization algorithm that assists in search for the optimal catalytic surface using a minimum number of virtual experiments. Theoretical results are validated with experiments.

EXAMPLE

Nitrogen Oxide Decomposition Catalyst Development

The invention may be better understood by illustration, considering an example. In this example, the CDE is used to identify and optimize commercially viable NO decomposition catalysts for use with lean-burn engines. These new catalysts enable the rapid large-scale commercial use of lean-burn engines and the realization of associated economic and environmental benefits. Currently, catalytic converters for traditional combustion engines are based on three-way catalysts (TWC's), which are incompatible with lean-burn engines.

The key technical barrier for a viable catalyst seems to be the higher affinity of oxygen for the catalytic site relative to the minority NO component—site competition. Since oxygen is present in much higher concentrations, the rate of NO decomposition is too slow. NO decomposition is thermodynamically favored over a wide temperature range of practical interest and the only reaction products are nitrogen and oxygen. The goal of the example of the present invention is aimed at identifying NO decomposition catalytic material that overcome the limitations of current catalysts and would be viable for commercial use.

A. Review of Past Catalyst Results

Despite extensive research efforts over the past 10–12 years, the currently known catalysts that decompose NO under the oxygen-rich conditions of the lean-burn engine still have severe limitations preventing their commercialization. These limitations include low activity, inhibition by high oxygen levels, poisoning by oxides of sulfur ($SO_x$), and inadequate hydrothermal stability. To put the required commercial catalyst performance into perspective, the average rate of NO decomposition (for a 80% removal level) needs to be $1.3 \times 10^{-4}$ mol $g^{-1}$ $min^{-1}$, calculated over the range of temperatures of operation (200–600° C.). This rate is about 50 times greaser than the estimated rate on the most active catalyst identified to date.

Recently studied catalysts fall into three general categories: transition metals, complex metal oxides, and metal ion-exchanged zeolites. The present example focuses on the better, but still far from adequately performing active catalytic components. Table 3 presents an overview of some of the better performing catalysts from past work.

TABLE 3

Potential NO Decomposition Catalysts Evaluated

| Catalyst | Advantages | Disadvantages |
|---|---|---|
| Cu-ZSM-5 (GM) | Appears to be active for both NO adsorption and decomposition | Poor hydrothermal stability—dealumination of the zeolite $SO_2$ poisoning |
| Fe-ZSM-5 | Appears to be active for both NO adsorption and decomposition | Poor hydrothermal stability—dealumination of the zeolite $SO_2$ poisoning $NO_2$ formation |
| Precious metals | Good hydrothermal stability Less sensitive to $SO_2$ poisoning | $NO_2$ formation |
| Pt/alumina | Less sensitive to $SO_2$ poisoning | $NO_2$ formation |
| Co oxide | | $SO_2$ poisoning |
| Fluorite and Brownmillerite (Eltron Research) | Up to 100% NO removal High concentration of O vacancies active for NO adsorption and decomposition | Seems to rely on exhaust gas CO and HC for NO removal Work done with no $O_2$ present |
| erovskite | Molecular modeling study done with performance testing (Japan) | Low NO decomposition activity |

TABLE 3-continued

Potential NO Decomposition Catalysts Evaluated

| Catalyst | Advantages | Disadvantages |
|---|---|---|
| WO$_3$ + Pt/alumina (Ford) | WO$_3$ has a positive effect on NO removal Test was done with SO$_2$ present | Best results were not up to desired 80% removal level Life information not reported Reduction may significantly contribute to NO removal since CO and HC are present |

The problem of hydrothermal stability affects most zeolite based catalysts, especially Cu-ZSM-5, as set forth in M. Iwamoto and H. Hamada (*Catal. Today*, 10, 57 (1991)). The zeolite catalysts are active for NO decomposition but they are prone to dealumination and loss of crystallinity at high temperatures (above 973 K) in the presence of water vapor (typically comprising 8–10% of the exhaust). Hence, Cu-ZSM-5 is unlikely to be stable enough to pass the durability test of the FTP (Federal Test Procedure), as set forth in J. N. Armor (*Catal. Today*, 26, 99 (1995)). Furthermore, SO$_2$ poisons Cu-ZSM-5. Since the hydrothermal stability and poisoning problems of ZSM-5 based catalysts still exist despite extensive efforts to improve them, the present inventors focused initially on metal and metal oxide catalytic material as opposed to zeolite-based systems. However, Cu-ZSM-5 is used as a reference catalyst in the development of our models in order to understand the properties of the active Cu species.

Noble-metal catalysts are active, as evidenced by their proven performance in the TWCs, but they do not have sufficient NO decomposition activity for lean-burn engine application without serious modification. Supported noble-metal catalysts resist SO$_2$ poisoning better than Cu-ZSM-5 apparently because of their ability to oxidize the SO$_2$ to SO$_3$.

B. Microkinetic Analysis

The observed rate of NO decomposition on Pt is proportional to (NO)/(O$_2$). The reaction is strongly inhibited by O$_2$, which competes for adsorption sites with NO. In addition, the presence of O$_2$ in the feed leads to the oxidation of the Pt surface, and its reconstruction, at high temperatures. The oxidized surface is less active than Pt. The observed rate expression on oxidized Pt resembles that observed on bulk metal oxides, CuO, NiO, Co$_3$O$_4$, and Fe$_2$O$_3$. On oxides the NO decomposition sites would be oxygen vacancies.

Amirnazmi and Boudart (J. of Catalysis 39, 383–394 (1975)) proposed the following mechanism:

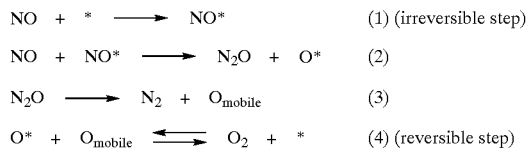

Assuming that step (1) is the rds, step (4) is quasi-equilibrated, and O* is the most abundant intermediate, this mechanism leads to the rate expression:

rate=$k_1$(NO)/(1+K$_4$O$_2$)~$k$/K(NO)/(O$_2$) with $k$=$k_1$ and K=K$_4$ (Eq. 1)

This mechanism invokes the formation of a mobile oxygen atom. N$_2$O is observed as product of NO decomposition at low temperatures on Pt Another possible mechanism for NO decomposition on metals involves the dissociation of adsorbed NO in adsorbed nitrogen and oxygen:

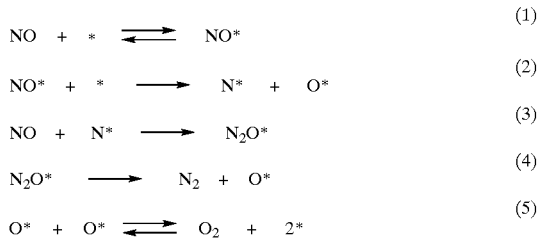

One can derive a similar rate the following rate expression, rate=$k_2$K$_1$(NO)/(1+{K$_5$(O$_2$)}$^{0.5}$)$^2$~$k$/K(NO)/(O$_2$) with $k$=$k_2$K$_1$ and K=K$_5$ (Eq. 2)

assuming that step (2) is the rds, steps (1) and (5) are quasi-equilibrated, and O* is the most abundant surface species. There is no need to invoke mobile oxygen in this case. Based on this preliminary kinetic analysis, a more active catalyst would require an increase in k or a decrease in K. In both mechanisms, decreasing the heat of adsorption of O$_2$ should result in a decrease in K. This analysis points to the oxygen binding energy as a key descriptor.

Figure 4A:
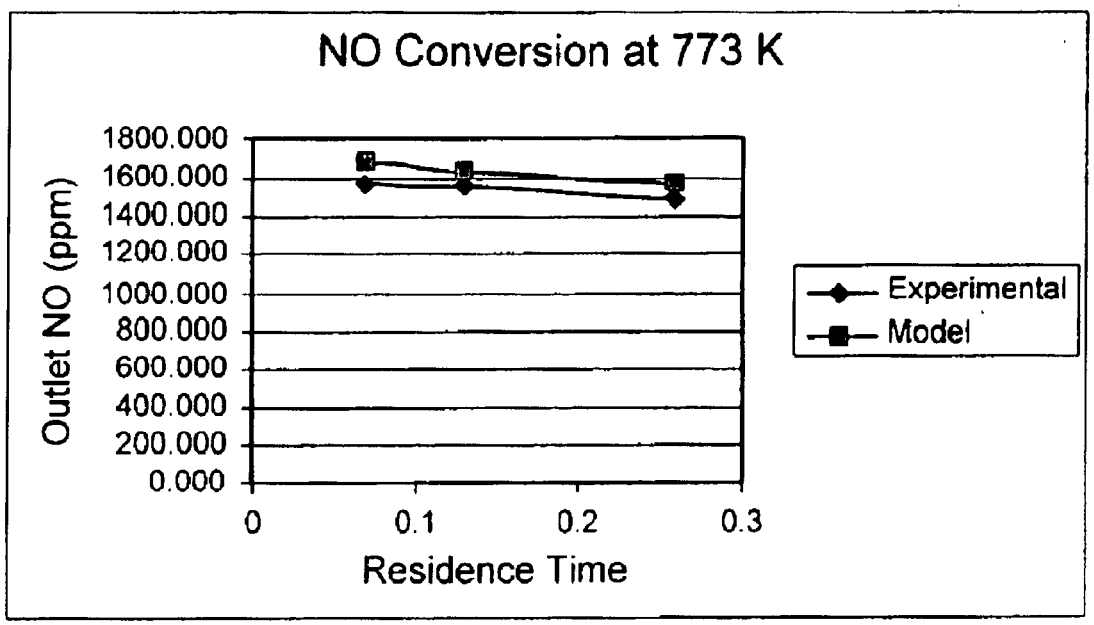
FIGS. 4a through 4c illustrate exemplary results of microkinetic analysis for NO decomposition on $Pt/Al_2O_3$ catalysts using the present invention.
Figure 4B:
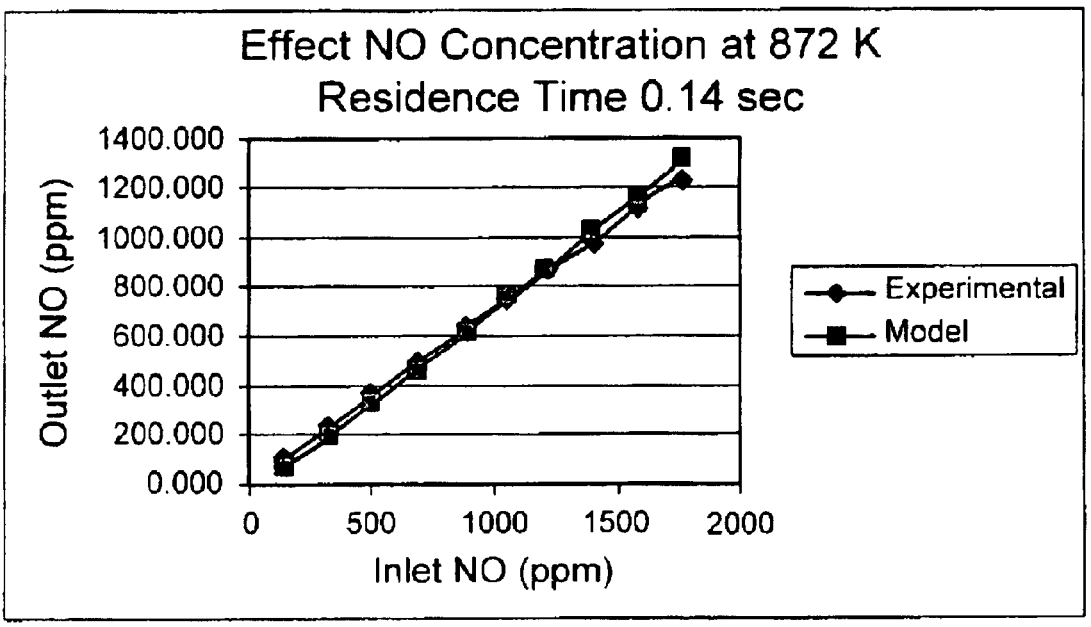

At high temperature N$_2$O is no longer observed as a product. A simpler mechanism was studied in more detail with microkinetic modeling to assess whether it could explain experimental results collected on 5 wt % Pt/alumina catalyst. The data were collected in a fixed-bed reactor at atmospheric pressure, temperature between 773 and 913 K, concentration of NO between ~200 and 1760 ppm, and with 0% or 1% O$_2$ in the reactor feed stream. Exemplary data points are illustrated in FIGS. 4a and 4b.

The reaction mechanism includes four steps:

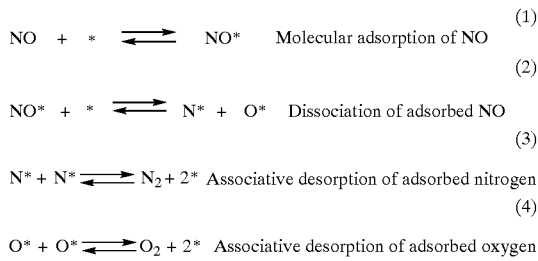

Four parameters are required for Steps 1, 3, and 4 of the reaction scheme: (1) an entropy change to form the activated complex from a gas-phase species to an adsorbed species; (2) an enthalpy change to form the activated complex from a gas-phase species to an adsorbed species; (3) an entropy change to form a stable species on the surface; and (4) an enthalpy change to form a stable species on the surface. Parameters 1 and 2 determine the temperature dependent rate-constant for an adsorption step and parameters 3 and 4 determined the equilibrium constant for that given step. Step 2 requires only two parameters: (1) an entropy change to form the activated complex for the forward step; (2) an enthalpy change to form the activated complex for the forward step. The equilibrium constant for step 2 is determined from the gas-phase thermodynamics of the overall reaction to convert NO to N$_2$ and O$_2$ [2NO ☐N$_2$+O$_2$]. The model utilizes thermodynamics properties of gas-phase reactants and products that are calculated using the entropies, enthalpies, and heat capacities such as those published in Yaw's (Yaws, No. 35 (1999)).

The reaction scheme requires fourteen parameters to describe the catalytic kinetics. The number of parameters may be reduced further with the following assumptions.

1. The pre-exponential factors for the adsorption steps (forward of step 1 and reverse of step 3 and 4) are calculated from collision rate theory assuming a sticking coefficient of 1.0. Accordingly, the pre-exponential factors for these steps are given by:

$$A\left(\frac{1}{atm\ cm^2 s}\right) = \frac{1.0123 \times 10^6}{\sqrt{2\pi m k_B T}}$$

2. The pre-exponential factor for step 2 is determined assuming no entropy change between the adsorbed NO species and its activated complex.
3. Both N* and O* species are mobile species on the surface.
4. The energetics for step 3 are obtained from ab initio molecular modeling on Pt(100):
   Activation energy for reverse step 3: $E_{rev,3}$ =22 kJ/mol
   Enthalpy of reaction of step 3: $\Delta H_{TX,3}$ =34 kJ/mol
5. The activation barrier for forward step 1 is obtained from ab initio molecular modeling on Pt(100):
   $E_{for,1}$ =21 kJ/mol
6. The activation barrier for the forward step 4 is obtained from Andersson et al. (J. Phys. Chem. B., Vol. 103, p10433–10439, (1999)).
   $E_{for,3}$ =21 kJ/mol
7. Adsorbed NO* is an immobile species on the surface.
8. The heat of $O_2$ adsorption is a function of adsorbed O* coverage as proposed by Andersson et al:
   Enthalpy of reaction of step 4: $\Delta H_{TX,4} = \Delta H_{zero\ coverage}$ $(100 - \alpha\Theta_{O*})$ where
   the heat of adsorption of $O_2$ at zero coverage is obtained from molecular modeling on Pt(100), $\Delta H_{zero\ coverage}$ =290 kJ/mol
   α is a scaling factor between 0 and 100
   $\Theta_{O*}$ is the fractional coverage of adsorbed oxygen.

With these assumptions, four parameters are adjustable in the fitting of the experimental data. Their fitted values are:
$\Delta H_{rx,3}$=−135.0 kJ/mol
$E_{for,2}$=142.0 kJ/mol
α=29.5
$\Delta S_{rx,2}$ =−28.2 J/(mol.K)

Figure 4C:
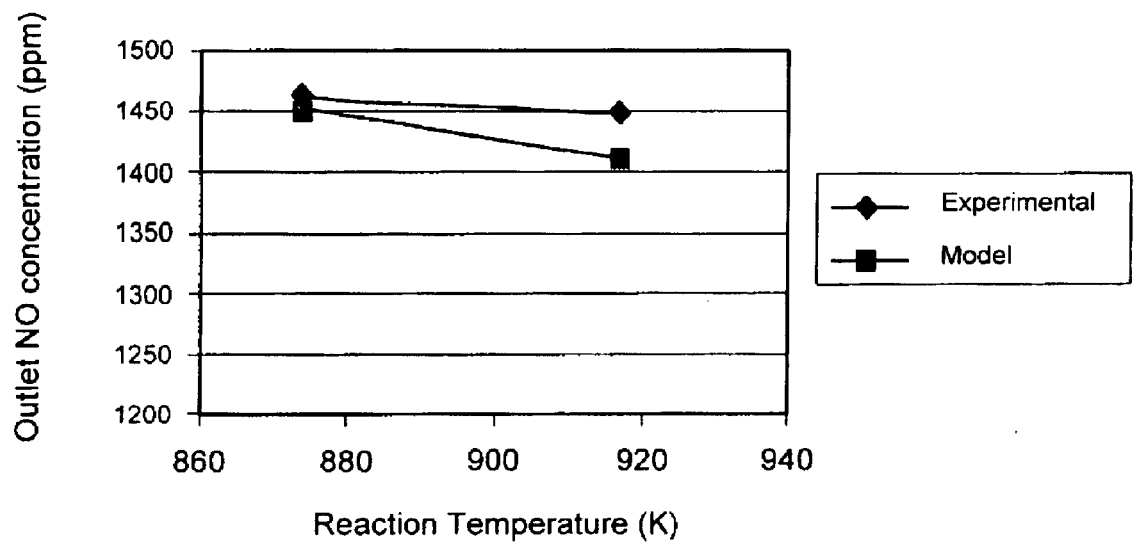

The reaction scheme and corresponding parameters describe reasonably well the experimental data in the absence of oxygen in the reactor inlet (FIGS 3a and 3b). This model explains quite well the observed changes in the rate of NO decomposition with changing inlet NO concentrations. When $O_2$ is added to the feed, the model over predicts the rate of NO decomposition (an example of which is illustrated in FIG. 4c) suggesting that additional data are needed to adjust the coverage dependence of the heat of $O_2$ adsorption.

The values of the adjustable parameters were analyzed for reasonableness. Molecular modeling calculations show that the heat of NO adsorption decreases with increasing coverage of NO and $O_2$. The lowest value is −165 kJ/mol at combined coverage of NO and O equal to 0.75. However, this value does not extend to the high oxygen coverage predicted by the model (over 90% coverage by adsorbed oxygen). Accordingly, the lower heat of adsorption calculated by the model for step 1 is reasonable. The forward activation energy for step 2 is higher than the 107 kJ/mol value predicted by molecular modeling on Pt(100), but again the latter value is valid at low coverage, and an increase in activation barrier is expected as coverage increases.

A subsequent sensitivity analysis showed that the overall rate was most sensitive to the heat of adsorption of oxygen (step 4) followed by the activation energy for the dissociation of adsorbed NO (step 2). These parameters are two most important descriptors suggested by this analysis. More complex mechanisms need be investigated in a similar fashion to explain the observed formation of $N_2O$ as low temperatures.

C. Identify Key Catalyst Properties

Based on the previous microkinetic analysis, oxygen binding energy is a key property affecting activity. In order to confirm this hypothesis, we attempted to correlate k/K with a measure of the oxygen binding energy, using published data for various catalytic systems. There is precedent for such an approach. The logarithm of rate constants of $N_2O$ decomposition and $O_2$ exchange at a given T on many oxides correlate linearly with each other and with the lattice parameter of these materials for each crystal structure. Since the rate-determining step in the exchange reaction is the desorption of $O_2$, the rate constant for $N_2O$ decomposition depends on the heat of adsorption of $O_2$ (assuming non-activated $O_2$ adsorption), which in turn depends on the metal-oxygen distance of the oxide. By analogy with these results, a correlation between k/K and the binding energy of oxygen could exist for NO decomposition. Using Equation. 3, values of k and K can be obtained from the plot of 1/r versus $[O_2]$ at a given T.

$$1/r = (1/k[NO]) + \{K/(k[NO])\}[O_2] \quad \text{(Eq. 3)}$$

Published values of k and K for Pt/$Al_2O_3$(0.6 wt % Pt, 3.7% dispersion) and various oxides at 973K may be used (such as those published in Amirnazmi and Boudart, J. of Catalysis 39, 383–394 (1975)). Values of k and K may be estimated from published variations of $1/v_t$ with $[O_2]$ at 773K for Cu-ZSM-5(such as Si:Al=26, Cu:Al=0.83, Cu content: 4.9× $10^{-4}$ mol $g^{-1}$, as published in Y. Li and W. K. Hall *J. Catal.*, 129, 202 (1991)). Values of k were calculated assuming a site density of 1.19×$10^{15}$ $cm^{-2}$ for Pt and $10^{15}$ $cm^{-2}$ for oxides. For the oxygen binding energy, measured by ($-\Delta H_{a, o_2}$), one may use the enthalpy of formation of the oxide in the case of oxide materials (such as that published in CRC Hanbook of Chemistry and Physics, $74^{th}$ ed., D. R. Lide, CRC Press (1993)). For Pt, one may use the energy of desorption of $O_2$ at high coverage because Pt does not form a stable oxide at those temperatures. For Cu-ZSM-5, one may used the enthalpy of the release of $O_2$ from $Cu_2^+(O^{2-})$ to $Cu^+$, such as that calculated by the Density Functional Theory (DFT) quantum chemical methods (Bell et al., J. Phys. Chem. 100, p17582–17592 (1996)). The values of k and K are summarized in Table 4.

TABLE 4

Kinetic Parameters for Various Catalysts at Two Temperatures

| | T (K) | | | | | | | |
|---|---|---|---|---|---|---|---|---|
| | 773 | | | | 973 | | | |
| Catalyst | $\Delta H$ (kJ mol$^{-1}$) | K (atm$^{-1}$) | k (cm$^3$ mol$^{-1}$s$^{-1}$) | k/K (atm cm$^3$ mol$^{-1}$s$^{-1}$) | $\Delta H$ (kJ mol$^{-1}$) | K (atm$^{-1}$) | k (cm$^3$ mol$^{-1}$s$^{-1}$) | k/K (atm cm$^3$ mol$^{-1}$s$^{-1}$) |
| Pt/Al$_2$O$_3$ | −201.0 | 2159.4 | 60200 | 27.9 | −201.0 | 360 | 758823 | 2107.8 |
| Co$_3$O$_4$ | −416.2 | 367.1 | 414 | 1.1 | −403.9 | 90 | 722 | 8.0 |
| CuO | −274.4 | 496.7 | 288 | 0.6 | −257.5 | 130 | 834 | 6.4 |
| Fe$_2$O$_3$ | — | — | — | — | −502.7 | 60 | 19 | 0.3 |
| NiO | — | — | — | — | −401.3 | 110 | 30 | 0.3 |
| Cu-ZSM-5 | −163.2 | 63.5 | 16396 | 258.2 | — | — | — | — |

Figure 5:
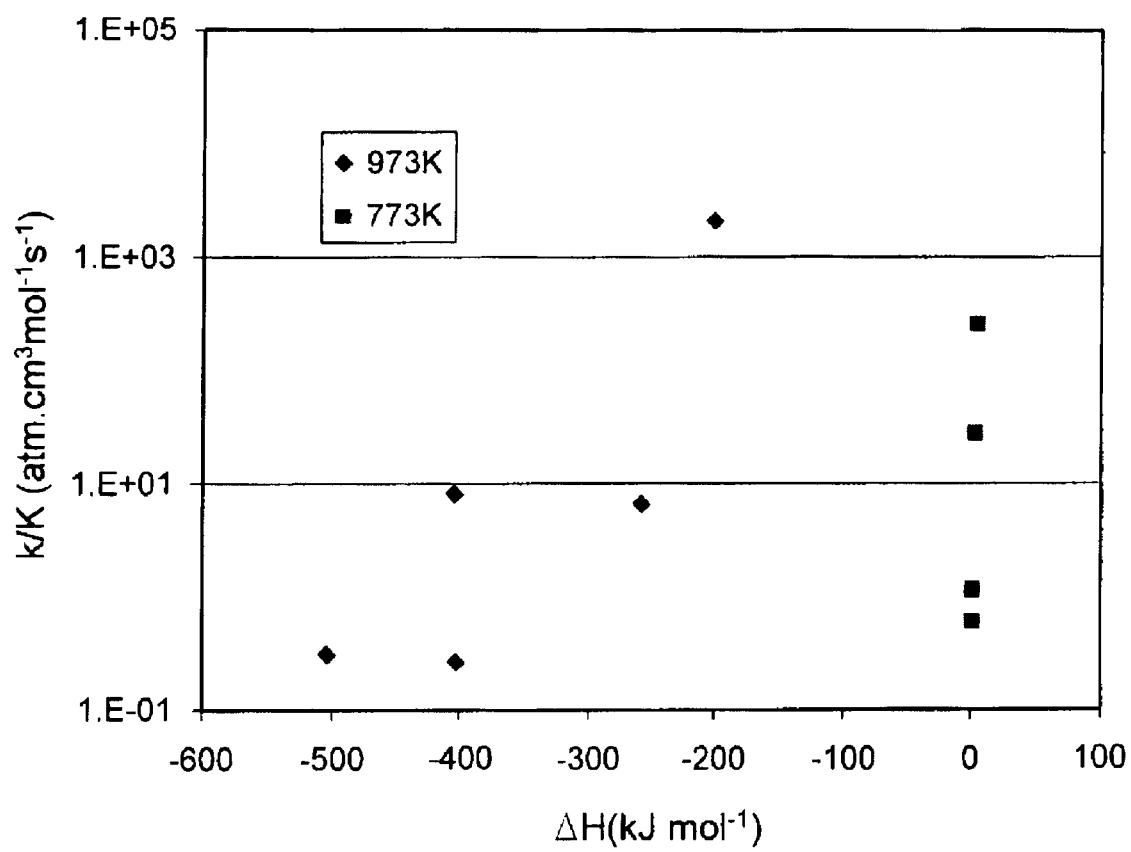
FIG. 5 is a plot of the apparent rate constant for NO decomposition versus oxygen affinity for various catalysts at two temperatures, in accordance with the example started in FIGS. 4a through 4c.

The variation of k/K with ΔH at 773K and 973K are shown in FIG. 5. Although the number of data points is limited, k/K increases as ΔH increases at both temperatures. Catalysts NiO and CuO do not fit the trend well.

As ΔH increases further (or the oxygen binding energy decreases), the rate of NO decomposition should decrease. Since NO and O$_2$ compete for adsorption on the same sites of these catalysts, as the affinity of these sites for oxygen decreases, their affinity for NO should eventually do too. Thus, an optimal value of ΔR likely exists and a site with such oxygen affinity should in principle have higher activity. Based on the data of FIG. 4, materials with ΔH>∼−200 kJ/mol should be investigated further in the next cycle of experiments.

Another complementary approach for the identification of important materials descriptors for this reaction is the use of machine learning and pattern recognition techniques to unearth relationships between materials properties, preparation and process parameters (i.e., synthesis method, raw materials, drying temperature, etc.) and materials performance parameters. For example, using literature experimental values of NO decomposition activity and activation energy on a series of oxide materials and a list of 21 tabulated properties of the oxides or of their respective metallic element, we applied recursive partitioning to unearth relationships between dependent and independent variables as well as between dependent variables. This also allowed us to identify independent variable with redundant information. The variables are shown in Table 5.

TABLE 5

| Variable | Description of Oxide M$x$O$y$ | Type |
|---|---|---|
| X1 | Atomic Number | Discrete |
| X2 | Oxide Formula | Discrete |
| X3 | Group of Element M | Discrete |
| X4 | Melting Point of Oxide (° C.) | Continuous |
| X5 | Observed Activation Energy for O2 Exchange, E1 (kcal/mol) | Continuous |
| X6 | Observed Activation Energy for N2O Decompostion, ENd (kcal/mol) | Continuous |
| X7 | Heat of Formation of Oxide, −ΔH°$_{298}$*10$^{-6}$ (kJ/mol O2) | Continuous |
| X8 | Atomic Radius of M (Ang.) | Continuous |
| X9 | Covalent Radius of M (Ang.) | Continuous |
| X10 | Magnetic Succeptibility (E−06 cgs) | Continuous |
| X11 | Electronegativity of Cation Mn+ | Continuous |
| X12 | First Ionization Potential of M (V) | Continuous |
| X13 | Electric Conductivity of M (E+06/ohm · cm) | Continuous |
| X14 | Thremal Conductivity of M (W/(K · cm) | Continuous |
| X15 | Polarizability of M (E−24 cm3) | Continuous |

TABLE 5-continued

| Variable | Description of Oxide M$x$O$y$ | Type |
|---|---|---|
| X16 | Refraction Index of Oxide, RI | Continuous |
| X17 | Polarizability of Oxide (E−24 cm3) | Continuous |
| X18 | Polarizability of Oxygen Anion (cm3) | Continuous |
| X19 | Ionization Energy of Electron in Oxide (∼1/X16$^4$) | Continuous |
| X20 | Bulk Structure of Oxide | Discrete |
| Y1 | Log[Observed Rate Constant at 873 K and 200 torr NO, k (cm − 2 · s − 1)] | Continuous |
| Y2 | Observed Activation Energy for NO Decomposition, Eo (kcal/mol) | Continuous |

The dependent variables are Y1 and Y2 and the independent variables are X1 through X21. There are no independent variables from the catalyst preparation or testing process in this example. The input data is shown in the Table illustrated in FIG. 6. Results of the recursive partitioning analysis are shown in Tables 7a and 7b. Tables 7a and 7b—Average Independent Variable (Descriptor) Usage Frequency in the Construction of 1000 Trees TABLES 7a and 7b Average Independent Variable (Descriptor)
Usage Frequency in the Construction of 1000 Trees

| Y1 | | Y2 | |
|---|---|---|---|
| Independent Variable | Total Frequency (%) | Independent Variable | Total Frequency (%) |
| X5 | 31.3% | X5 | 61.9% |
| No split | 30.1% | X6 | 23.1% |
| X20 | 9.4% | X19 | 12.7% |
| X17 | 9.1% | No Split | 0.7% |
| X3 | 4.3% | X4 | 0.5% |
| X7 | 4.0% | X1 | 0.3% |
| X8 | 2.5% | X17 | 0.3% |
| X4 | 1.7% | X8 | 0.1% |
| X15 | 1.4% | X20 | 0.1% |
| X10 | 1.3% | X13 | 0.1% |
| X1 | 1.2% | X10 | 0.1% |
| X13 | 1.2% | X16 | 0.1% |
| X16 | 0.9% | Total | 100.0% |
| X18 | 0.5% | | |
| X19 | 0.4% | | |
| X6 | 0.3% | | |

TABLES 7a and 7b-continued

Average Independent Variable (Descriptor)
Usage Frequency in the Construction of 1000 Trees

| Y1 | | Y2 | |
|---|---|---|---|
| Independent Variable | Total Frequency (%) | Independent Variable | Total Frequency (%) |
| X12 | 0.2% | | |
| X9 | 0.1% | | |
| X14 | 0.1% | | |
| Total | 100.0% | | |

In this example, the most important descriptor that describes both Y1 and Y2 is clearly X5, the apparent activation barrier for $O_2$ exchange reaction. This confirms the finding by Winters et al. that the fact that the ability of the material to desorb oxygen is critical. In the case of Y1, X5 is the only significant independent variable that describes the data; since the probability of no-split ranks second, all other variables are statistically insignificant. This is due to the small size of the dataset. In the case of Y2, X6, the measured apparent activation barrier for $N_2O$ decomposition, and X19, the ionization energy of an electron in a surface oxygen ion vacancy, are significant as well. Decomposition of NO and decomposition of $N_2O$ share common elementary steps such as the adsorption of NO, the desorption of $O_2$, and possibly others. Also $N_2O$ is observed as a product of NO decomposition on Pt at low temperatures. The importance of X19 suggests that the chemisorption of NO is connected with the transfer of an electron from the material to the NO molecule. The lower X19 is, the stronger the chemisorption of NO and also the ability of the NO to dissociate will be.

Figure 7:
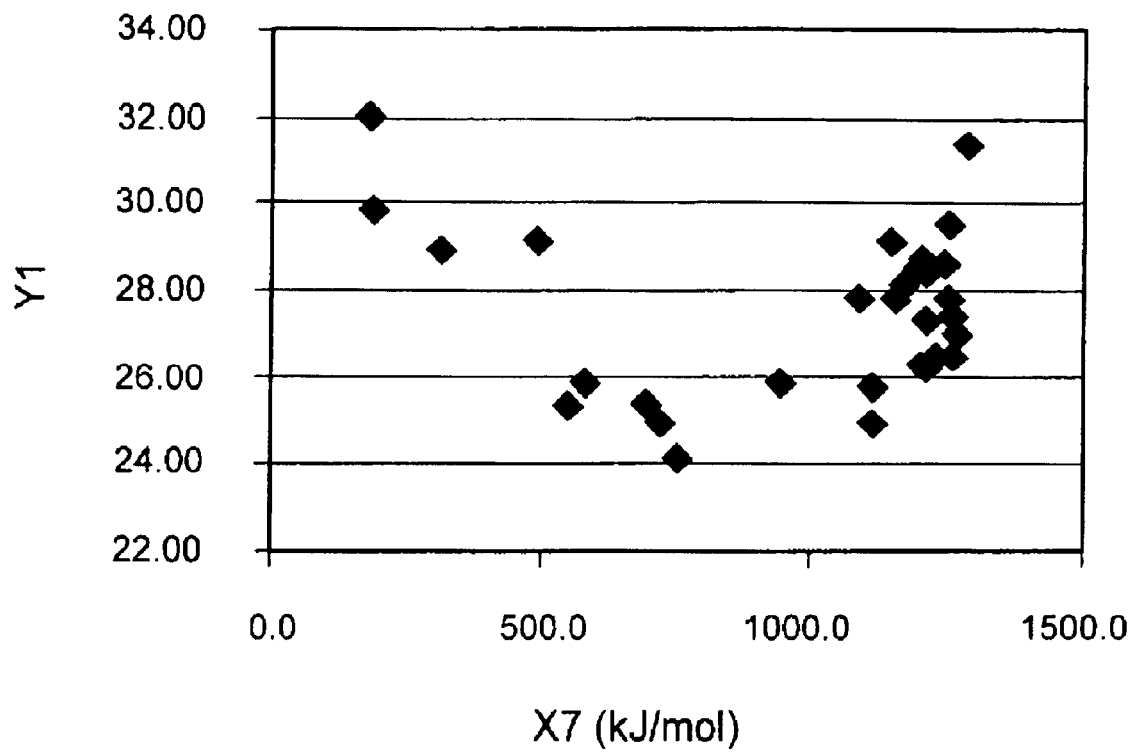
FIG. 7 is a plot of the apparent rate constant for NO decomposition versus the standard enthalpy of formation of oxides, in accordance with the example started in FIGS. 4a through 4c.

The fact that X7, the standard heat of formation of the oxide, which is a proxy parameter for the oxygen biding energy, was not significant for either Y1 or Y2, prompts a closer examination of the data. In FIG. 7, Y1 is plotted against X7.

The materials can be classified in two classes: In class I materials, as X7 increases, Y1 decreases; and in class II materials, Y1 seems less sensitive to X7. Class I materials confirms the conclusions of the microkinetic analysis and FIG. 5. In class II materials, the rate of NO decomposition seems to increase with increasing X7, although there is more scatter in the data. Class II materials are generally non-reducible oxides that have strong oxygen binding energy. The reaction likely operates with a different mechanism on these materials. This points to another region of potential interest, materials with large X7 values, which requires further exploration.

In this example, recursive partitioning using ensemble of trees may also be effective in pointing to redundant independent variables that the user may not have rationalized in the variable selection. For example, thermal and electrical conductivity variables (X13 and X14 respectively) may be highly correlated. Variables X5 and X6 may also be found to be closely related which correctly suggests that the decomposition of $N_2O$ is also inhibited by adsorbed oxygen.

D. Guide Selection of Materials for Subsequent Cycle of Experiments (Virtual Screening)

In order to guide the experimental effort and minimize the number of experiments to be carried out, it is useful to pre-screen potential materials by calculating estimates of the critical kinetic and thermodynamic surface parameters (descriptors) that were identified previously; or more preferably by calculating estimates of the NO decomposition activity. This allows the scientist to look for trends in a class of virtual materials and to test the hypothesis put forward. Semi-empirical computational chemistry methods such as Extended-Huckel Theory that have been calibrated with first-principle molecular modeling results are useful for such parameter estimations because they are much faster than ab initio techniques and while they yield less accurate absolute calculation they generate accurate trends across materials classes. The estimated parameters can be used in a Monte-Carlo kinetic simulation, which takes into account kinetic elementary steps and the various surface sites, their concentration and their spatial arrangement.

Figure 8:
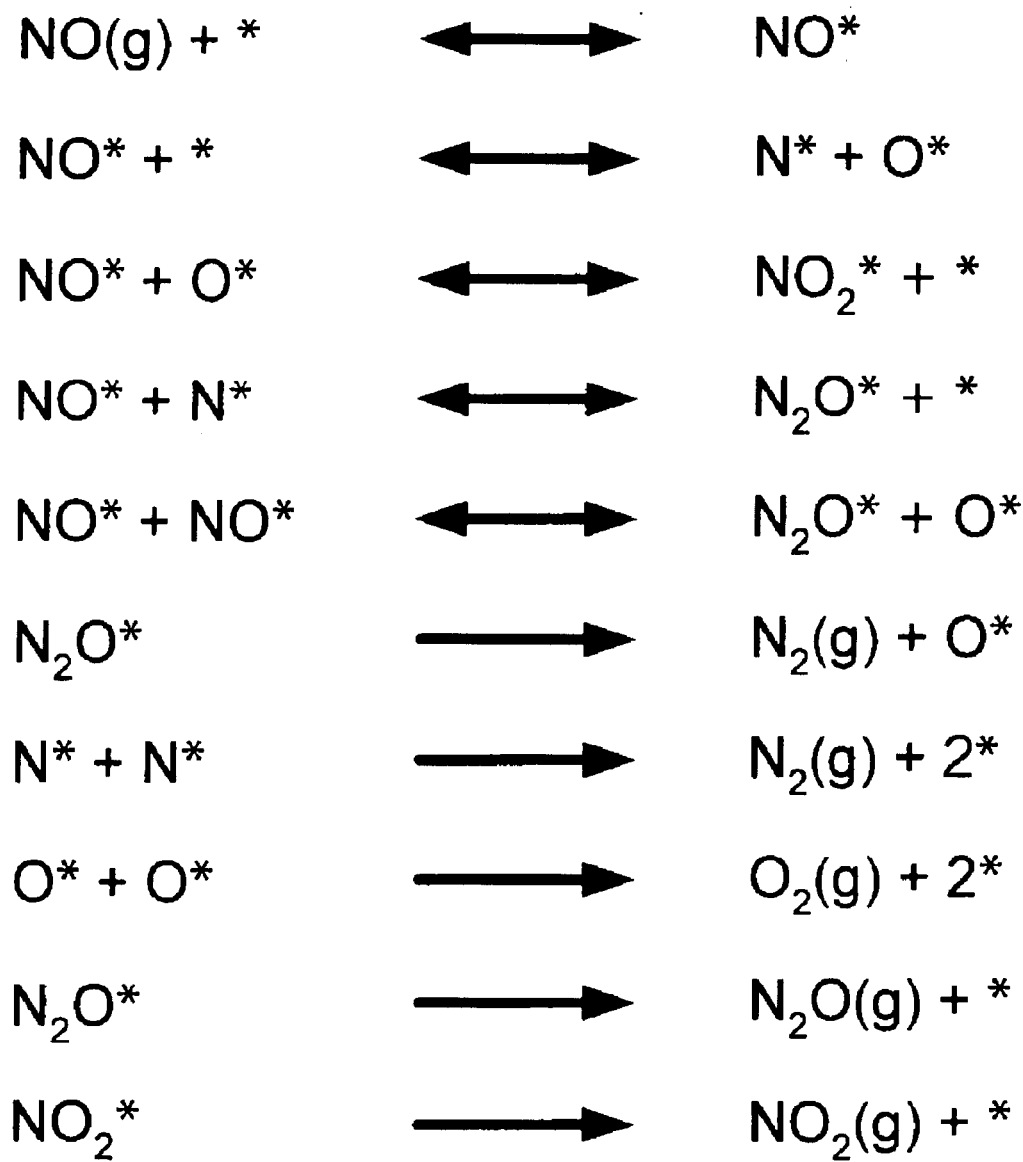
FIG. 8 is a list of elementary steps for NO decomposition and oxidation, in accordance with the example started in FIGS. 4a through 4c.
Figure 9:
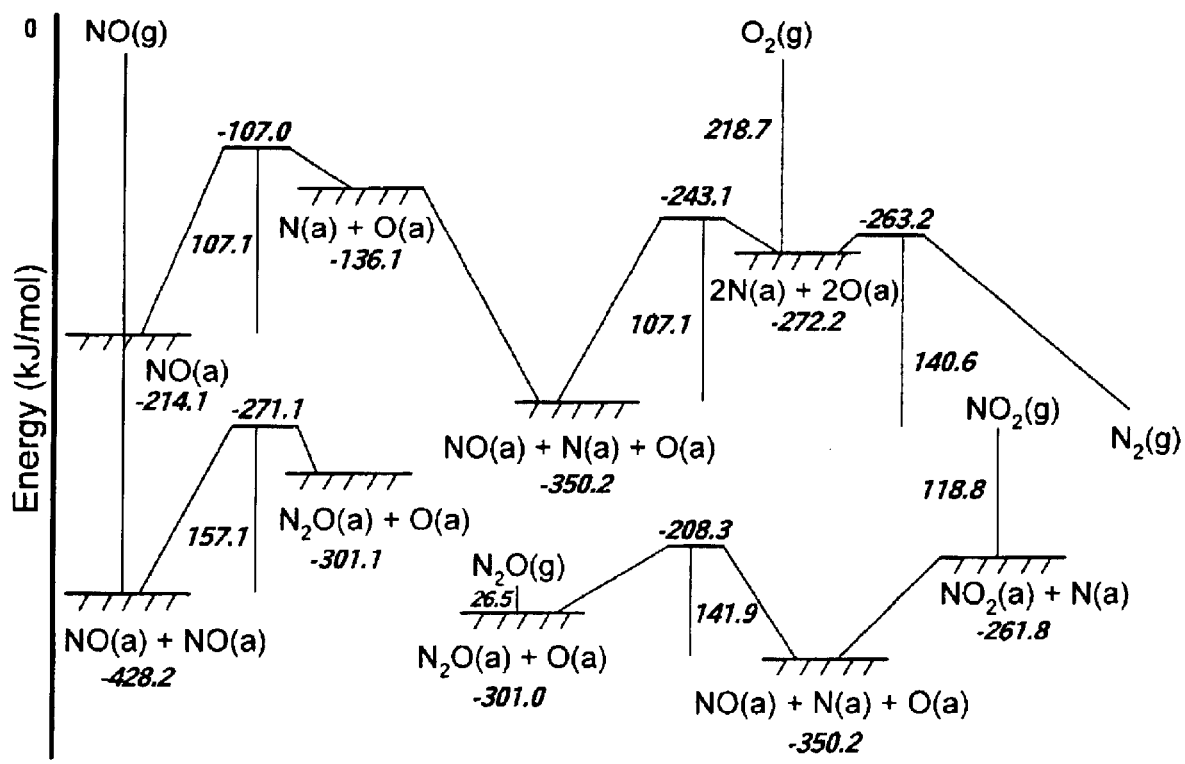
FIG. 9 is an energy diagram for the elementary steps listed in FIG. 8.
Figure 10:
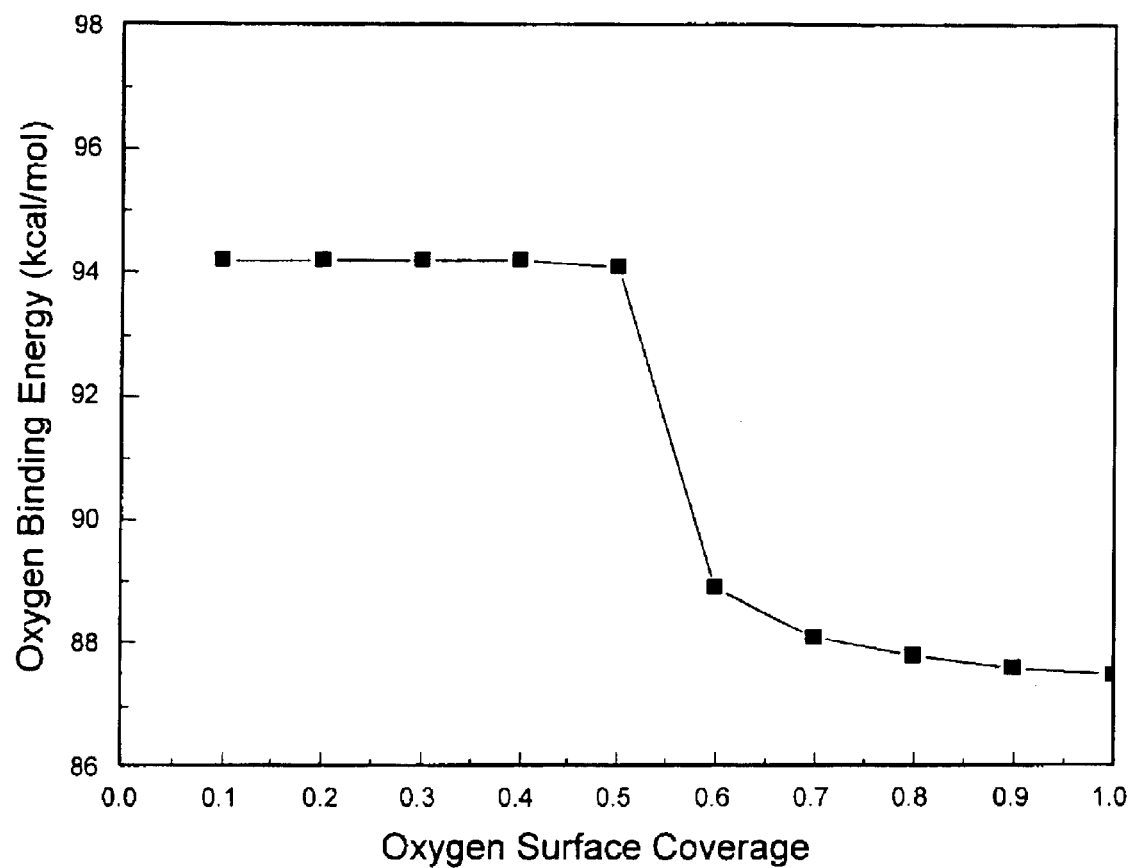
FIG. 10 is a plot of the calculated binding energy of adsorbed oxygen on Pt(100) as a function of coverage, in accordance with the example started in FIGS. 4a through 4c.

Such simulations may, for example, be carried out on Pt(100) and Rh(100) to illustrate the value and tremendous potential of this approach to catalyst discovery and development efforts. The elementary steps that would be allowed to take place on the metal surface in the simulation are listed in FIG. 8. The binding energies of the relevant adsorbed species, calculated using DFT, are shown in Table 8. Only the most probable adsorption sites are examined in this example. For example, nitrogen and oxygen adatoms will only occupy the bridge and hollow sites. Preferably, the atop sites would not be examined. The values for the most favorable adsorption sites are presented in italics in Table 8. The activation energies for the elementary steps on Pt(100) are shown in FIG. 9. For example the activation energy for the dissociation of NO on a bare Pt(100) surface was calculated at 107 kJ/mol. The effects of lateral interactions (or coverage) on the energies were calculated using two techniques. The through-surface interactions which occur via charge transfer between two adsorbates through the surface. These interactions were estimated using Bond Order Conservation (BOC) predictions and fitting the BOC parameters to representative DFT results. The through space adsorbate-adsorbate interactions include Van der Waals forces and static electronic interactions. They were predicted using the Merck Molecular Force Field Model. For example, the effect of oxygen coverage on the oxygen binding energy is shown in FIG. 8.

TABLE 8

Binding Energies of Adsorbed Species on Pt(100)

| Species | Atomization Energy | Atop | Bridge | 4-hold Hollow |
|---|---|---|---|---|
| NO | 671.5 | 136.6 | 214.3 | 157.8 |
| N | — | — | 403.1 | 414.4 |
| O | — | — | 394.0 | 359.4 |
| $N_2O$ | 1225.3 | 26.5 | 11.9 | — |
| $NO_2$ | 1073.4 | 118.8 | 74.4 | — |

The simulation tracks the occurrence of elementary physicochemical steps along with their corresponding kinetics to follow the fate of each individual molecule that adsorbs on the Pt surface. The kinetics for adsorption. desorption and all surface reaction steps enumerated in FIG. 8 are followed as a function of time and process conditions. All sites on the surface are explicitly modeled. This enables to capture the effect of the local composition as well as the atomic structure on the catalytic kinetics.

The simulations start by allowing first the surface to equilibrate with respect to the gas phase partial pressures of the reactants. Once the initial surface structure is equilibrated the surface reactions are allowed to take place.

Figure 11:
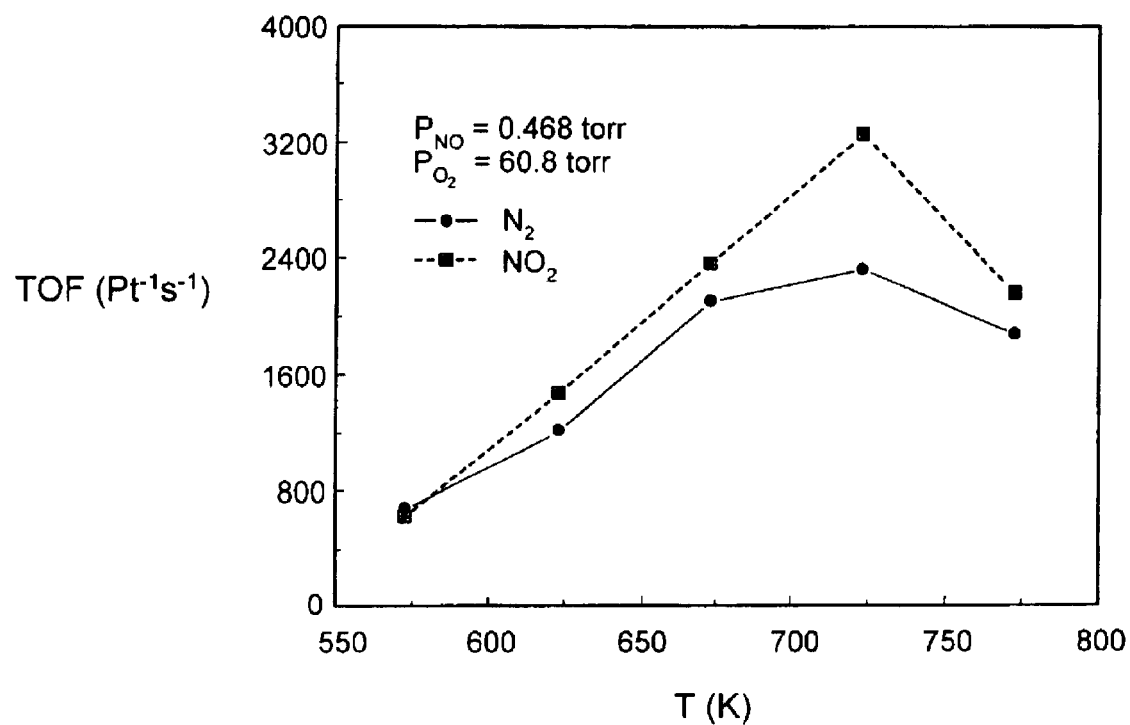
FIG. 11 is a plot of the calculated turnover frequencies of $N_2$ and $NO_2$ formation on Pt(100), in accordance with the example started in FIGS. 4a through 4c.
Figure 12:
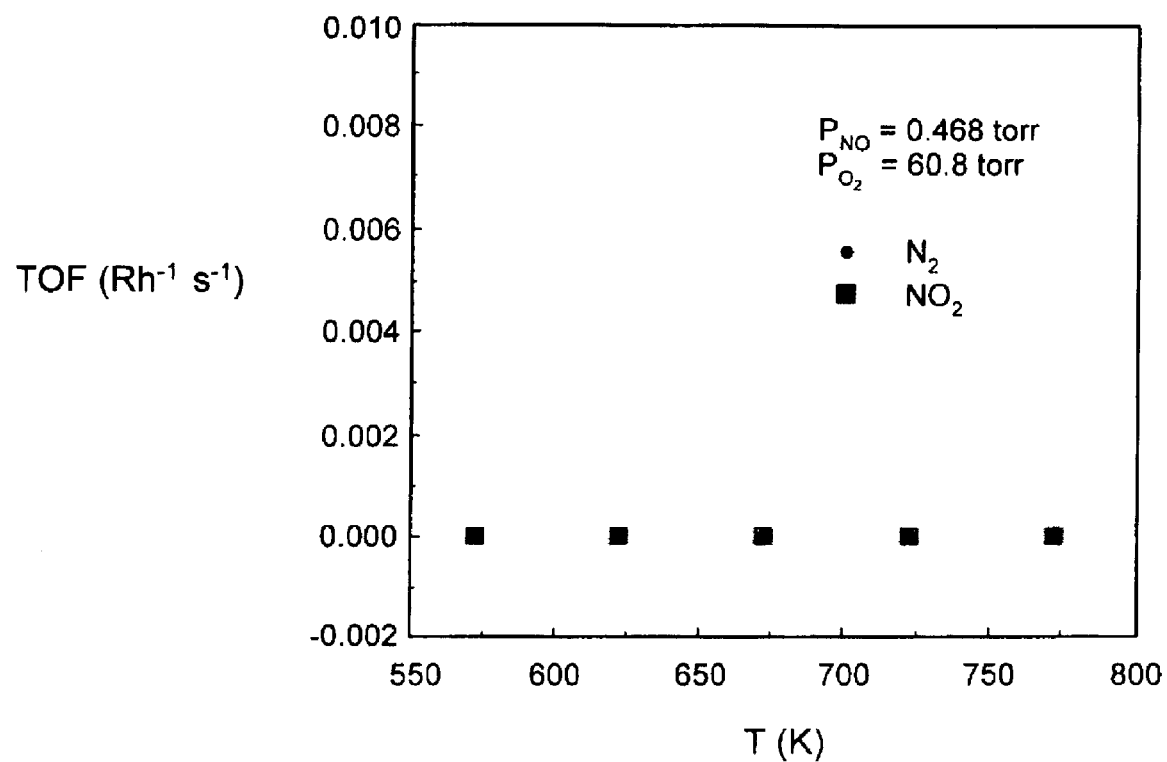
FIG. 12 is a plot of the calculated turnover frequencies of $N_2$ and $NO_2$ formation on Rh(100), in accordance with the example started in FIGS. 4a through 4c.

Subsequently, the simulation continues for some time to achieve the steady state. The number of product molecules that desorb can be directly counted, so that an explicit measure of the turnover frequency can be calculated and compared to experimental values. The simulation can then be run as a virtual experiment by changing the temperature, partial pressures, surface structure, and even the metals used. Using these calculated data, the turnover frequency (TOF) for steady-state formation of $N_2$ and $NO_2$ may be calculated on Pt(100) at several temperatures and $[O_2]$=60.8 torr and $[NO]$=0.468 torr (FIG. 11). Similar calculations may be performed for Rh(100). The binding energies are shown in Table 9 and the TOF values are plotted in FIG. 12 for Rh(100). The Monte Carlo simulation results show that Rh(100) is inactive for NO decomposition and NO oxidation because oxygen adsorbs strongly to the surface and inhibits NO adsorption and reaction.

TABLE 9

Binding Energies of Adsorbed Species on Rh(100)

| Species | Atomization Energy | Atop | Bridge | 4-hold Hollow |
| --- | --- | --- | --- | --- |
| NO | 671.5 | 219.6 | 263.8 | 256.6 |
| N | — | 353.6 | 475.4 | 547.8 |
| O | — | 376.8 | 474.4 | 496.7 |
| $N_2O$ | 1225.3 | 53.9 | — | — |
| $NO_2$ | 1073.4 | 177.4 | — | — |

Catalysts of Pt and Rh supported on γ-alumina may be synthesized and tested in a fixed-bed reactor for NO decomposition at 773 and 873K, [NO]=1.338 torr and $[O_2]$=0 torr. The catalyst properties and corresponding TOF values for $N_2$ formation are shown in Table 10. No $N_2$ O and $NO_2$ products were detected. The Pt catalyst was obtained from Alfa Aesar; the Rh catalyst was prepared by incipient wetness impregnation of a La Roche VGH-22 γ-alumina with an aqueous solution of $Rh(NO_3)_3$. The TOF values on Pt may be calculated from integrated NO conversion values assuming first order in NO, which may be verified experimentally. The oxygen inhibition need not be taken into account in this calculation. A quantitative agreement between the experimental and simulation results is not expected. The simulations may be carried out over model Pt(100) surfaces which contain distinct and active four-fold adsorption sites. The experiments may be performed on supported particles which likely contain a much more significant fraction of the more stable closed-packed surfaces. Simulation results run on the (111) surface indicate that this surface would be relatively inactive due to the NO dissociation barrier height which is greater than 200 kJ/mol. The actual measured rate over supported Pt particles is most likely some ensemble average from simulation results over both the Pt(100) and Pt(111) surfaces. The simulations over Pt(100) and Pt(111) surfaces therefore provide upper and lower bounds respectively for the actual experiments.

Although the predicted and measured TOF values for $N_2$ formation do not agree, the Monte Carlo simulation does predict the relative decrease in activity going from Pt to Rh surfaces.

TABLE 10

Pt and Rh catalyst properties

| Catalyst | Metal Content (weight %) | Metal Dispersion (%) | $N_2$ formation, TOF (s − 1) 773 K | 873 K |
| --- | --- | --- | --- | --- |
| Pt/Al2O3 | 4.8 | 29 | 0.0004 | 0.0015 |
| Rh/Al2O3 | 0.9 | 85.9 | 0 | 0 |

These results are useful as well to the microkinetic model as it provides energetic values as a function of coverage. This information is very valuable to the researcher who can focus experiments on more promising leads as predicted by the virtual screen. Virtual screening saves valuable experimental resources and provides insight into the surface chemistry. Additional surfaces of Pt and Rh and their alloys can be screened with this method.

Materials Search Strategy Based on Initial Cycle of CDE

Figure 13:
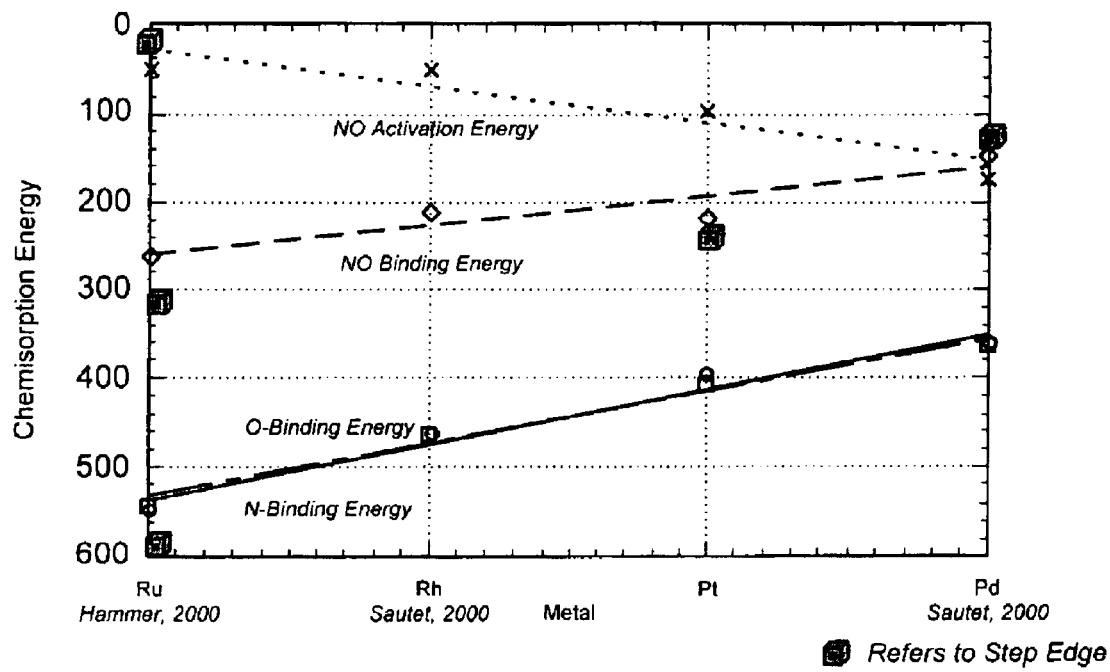
FIG. 13 shows Density Function Theory (DFT) calculated heats of adsorption for 0*, N*, and NO* and the NO activation barrier over several different transition metal surfaces, in accordance with the example started in FIGS. 4a through 4c.

The MC simulation, microkinetic analysis, and data mining results all show that both the NO activation energy and the heat of adsorption of oxygen are important in controlling the surface chemistry. To probe other materials, the researcher can use the scientific framework defined herein to define new material search strategies. The working hypothesis acts as an initial guide but will be refined as one proceeds through subsequent rounds of the testing and knowledge cycles. Ab initio DFT calculations, semi-empirical extended Huckel calculations, and literature data may be used to construct periodic trends, such as those illustrated in FIG. 13. FIG. 13 illustrates the challenge in finding a single active metal. The two parameters that appear to control the kinetics (the oxygen binding energy and the NO activation energy) are shown to be directly correlated. Although metals such as Pd and Cu bond oxygen much more weakly, they are not likely to be active enough to dissociate NO. Metals such as Rh and Ru, on the other hand, can readily dissociate NO but they tend to readily poison.

Based on the results from the initial run through the knowledge cycle, three new search strategies may be identified to circumvent the limitations found in FIG. 13. They include: 1) generation of active atomic structural ensembles; 2) alloy formation; 3) the formation of magnetic alloys.

Figure 14:
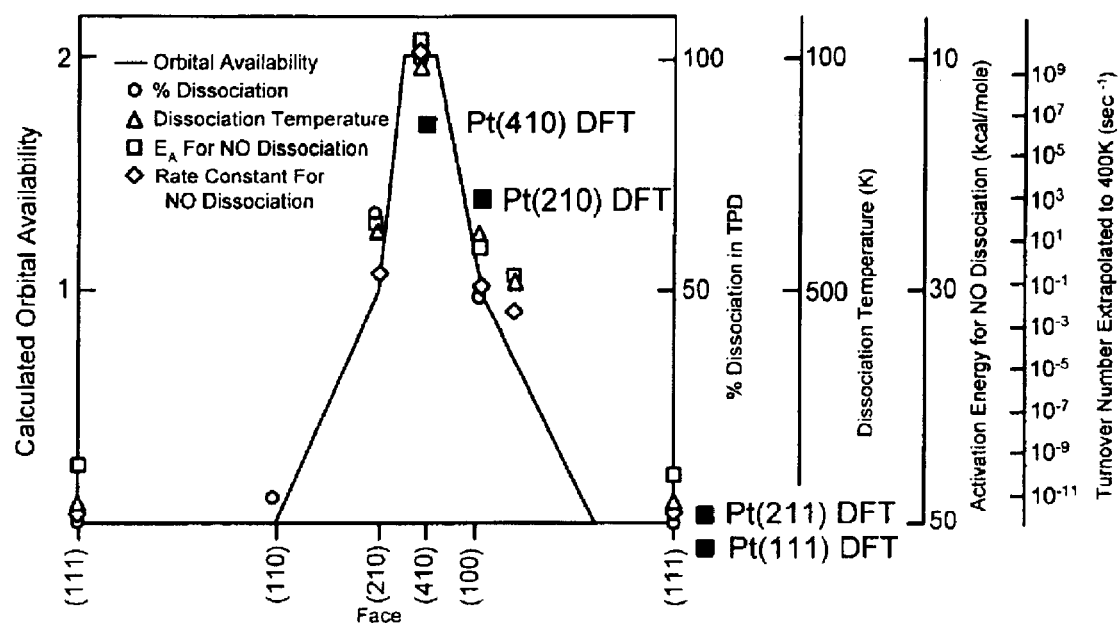
FIG. 14 represents the variations of the calculated NO activation energy as a function of the structure of ideal Pt single crystal surfaces, in accordance with the example started in FIGS. 4a through 4c.
Figure 15:
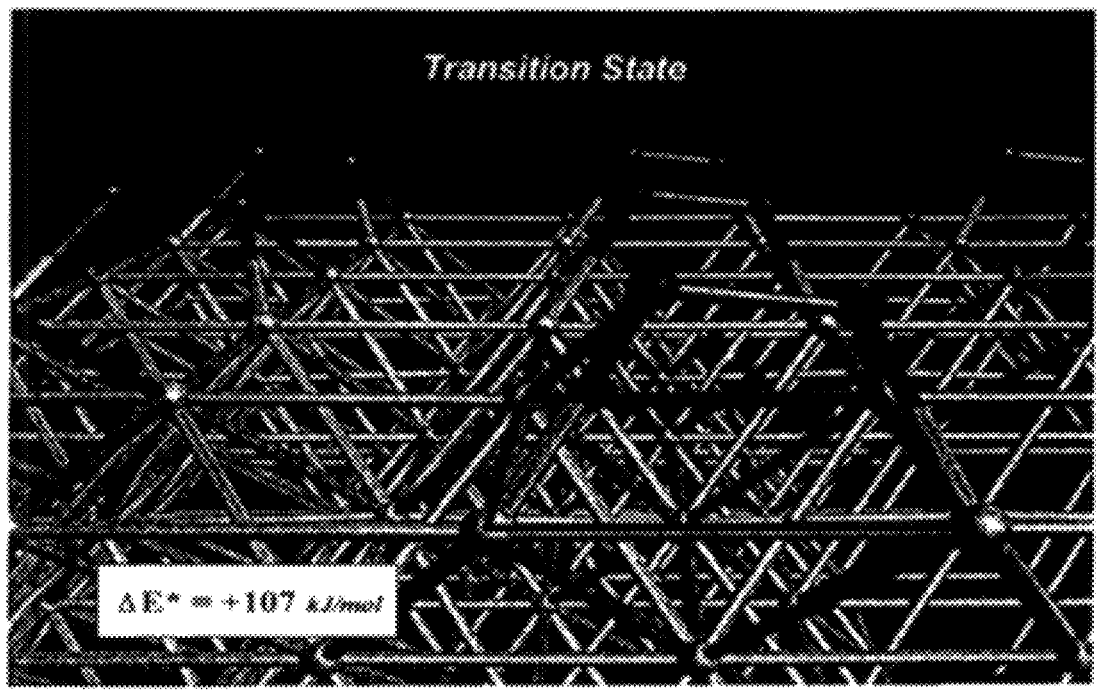
FIG. 15 shows the DFT calculated transition state for the activation of NO over Pt(100), in accordance with the example started in FIGS. 4a through 4c.

Initial quantum chemical results indicated that the specific atomic surface structure of the metal can greatly affect the nature of the transition state and hence the activation barrier for NO dissociation. FIG. 14, for example, shows the comparison of DFT and surface science results for the activation of NO over different ideal Pt surfaces. NO may be found to be inactive on the Pt(111) surface. The surface science results would suggest that the more open surfaces such as Pt(210) and Pt(410) can readily activate NO. The DFT results performed in the CDE confirm that the Pt(210) and Pt(410) are more active, but the activity increase is due not only to the increase in the surface corrugation but also to the unique structure of the 4-fold site. In addition to the Pt(410) surface, the Pt(210) and Pt(100) surfaces are also fairly active. The nature of square metal atom arrangement seems to be unique. It provides a special site whereby NO dissociates over the 4-fold hollow site in the center and produces N and O products which sit at neighboring bridge sites. It is important to note that DFT calculations for the NO dissociation on this 4-fold site show that the N and O in the transition state along with the resulting N* and O* surface species do not share any metal atom neighbors. The transition state is such that two Pt atoms stabilize N* and two other atoms stabilize O* (FIG. 15). The removal of metal atom sharing in both the transition states and the product states dramatically lowers the activation barrier. The 4-fold site is unique in that it will readily activate NO but should not be poisoned by the products. The previous MC simulations on Pt(100) confirm that effect. Indeed the calculated rate of NO decomposition on Pt(100) was much greater than the measured rate on supported particles. Modifiers that could stabilize this site would be of interest.

Bimetallics systems is a second class of materials that could lead to increased rate of NO decomposition based on the CDE hypothesis. Bimetallic systems provide a mean to optimize the M—O bond strength along with the activity. One method to vary the oxygen binding energy systematically is to alloy a group VIII metal with a group IB metal in order to form bimetallic particles. A good example is the Pd—Au system, where Au lowers the binding energy of oxygen leading to orders of magnitude increase in the rate of the $H_2O_2$ reaction. Group VIII metals have sites where $O_2$ has a higher affinity for the metal site than NO but the site is active for the catalytic decomposition of NO to $N_2$ and $O_2$. These noble metals are also good oxidation catalysts and this can lead to more complicated and offsetting chemistry such as the oxidation of NO to $NO_2$. Other modifiers could be used as well. Modifiers such as Sn and group VII elements have been used to modify the surface properties of group VIII metals in other reactions. There are indications in the literature that suggest that NO coupling can occur over PtSn alloys resulting in the formation of either $N_2$ O (g) or $N_2$ (g) and O*. This provides a route in which we can alter the dependence of NO activation and oxygen poisoning. NO coupling provides an alternative path to NO removal, which may not be as sensitive to oxygen surface coverage as direct NO dissociation.

A third possible strategy is the use of magnetic alloys. The details of the electronic structure of the reactant and the transition state suggest that the introduction of a second metal with specific magnetic properties may help to lower the NO activation barrier. NO is unique in that it already has one electron in an antibonding NO* orbital. Tuning the metal surface structure so that it can inject an extra electron into the NO* antibonding orbital would enable a low energy path to the activation of NO and minimize oxygen poisoning at the same time. Indeed, the activation barrier for NO dissociation on $Pd_3Mn(100)$ alloys is lower by 60–80 kJ/mol than the value on Pd(100). Manganese provides the appropriate magnetic centers to offer electrons to Pd. On the other hand, Pd would not be very susceptible to poisoning by oxygen.

E. Testing Cycle

Next, a library of proposed materials is synthesized and evaluated. Scaleable, high-throughput experimental methods are preferable as they allow more materials to be synthesized and tested under a broader process condition space and a much faster rate. This allows for the overall CDE cycle to be shorter and for the generation of enough data to increase the accuracy of the data-based models. A library of materials is created by varying composition, raw material suppliers, synthesis methods, or synthesis process parameters, or others. Both the dependent variables, i.e., the activity of NO decomposition and product selectivity and the key descriptors (independent variables) are quantified. The activity and selectivity are measured at several temperatures and several feed gas compositions, using steady-state or transient experiments, so that minimal kinetic information is available for meaningful comparison of materials. The oxygen binding energy is calculated from the measured energy of desorption of dioxygen by thermal desorption or other technique. The new data are then added to the knowledge repository and the CDE cycle is iterated.

Certain portions of the invention may be performed by an automated processing system. Viewed externally in FIG. 16, an exemplary computer system designated by reference numeral 101 has a central processing unit located within a housing 108 and disk drives 103 and 104. Disk drives 103 and 104 are merely symbolic of a number of disk drives which might be accommodated by the computer system. Typically these would include a hard disk drive and optionally one or more floppy disk drives such as 103 and/or one or more CD-ROMs, CD-Rs, CD-RWs or digital video disk (DVD) devices indicated by slot 104. The number and types of drives typically varies with different computer configurations. Disk drives 103 and 104 are in fact options, and they may be omitted from the computer system used in connection with the processes described herein. Additionally, the computer system utilized for implementing the present invention may be a stand-alone computer having communications capability, a computer connected to a network or able to communicate via a network, a handheld computing device, or any other form of computing device capable of carrying out equivalent operations.

The computer also has or is connected to or delivers signals to a display 105 upon which graphical, video and/or alphanumeric information is displayed. The display may be any device capable of presenting visual images, such as a television screen, a computer monitor, a projection device, a handheld or other microelectronic device having video display capabilities, or even a device such as a headset or helmet worn by the user to present visual images to the user's eyes. The computer may also have or be connected to other means of obtaining signals to be processed. Such means of obtaining these signals may include any device capable of receiving images and image streams, such as video input and graphics cards, digital signal processing units, appropriately configured network connections, or any other microelectronic device having such input capabilities.

An optional keyboard 106 and a directing device 107 such as a remote control, mouse, joystick, touch pad, track ball, steering wheel, remote control or any other type of pointing or directing device may be provided as input devices to interface with the central processing unit.

Figure 16:
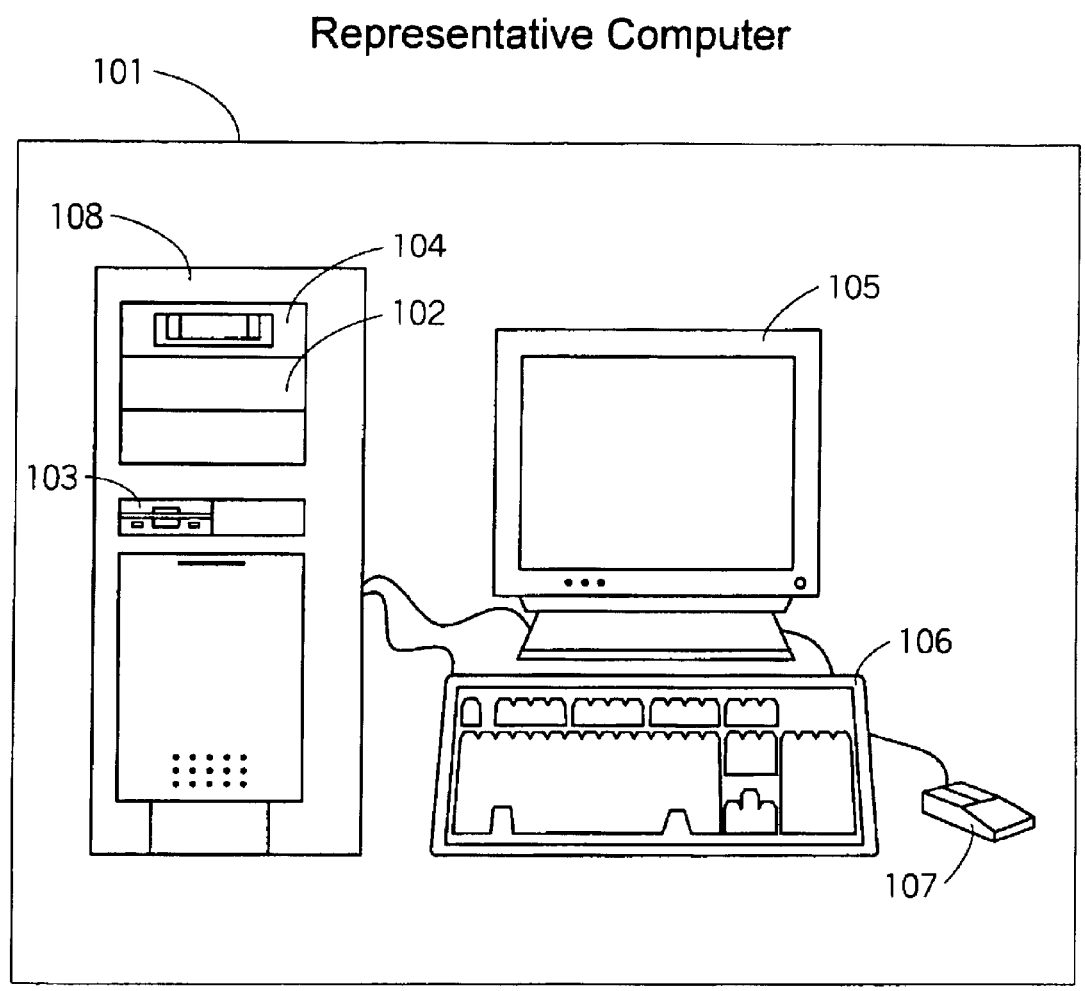
FIG. 16 illustrates an exemplary computer suitable for carrying out the automated functions of the present invention.
Figure 17:
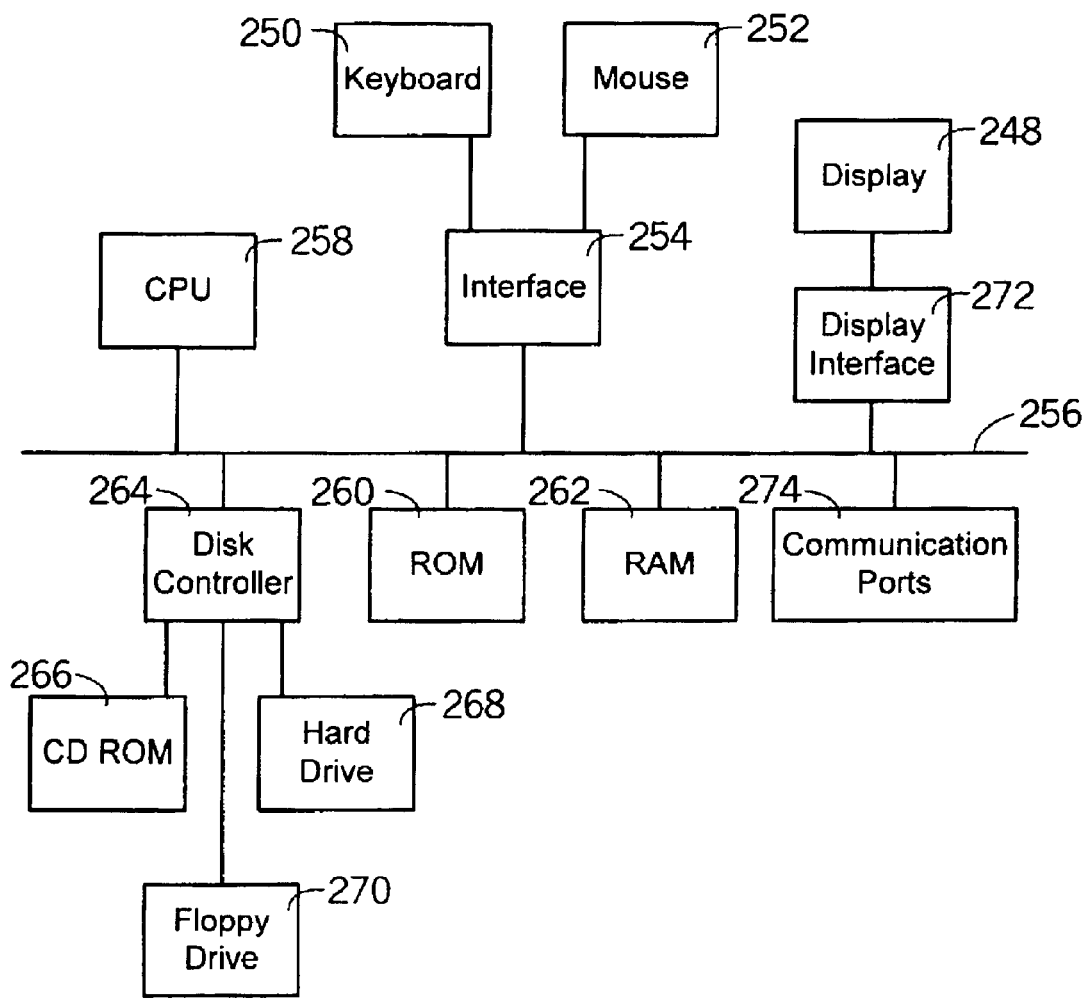
FIG. 17 illustrates the internal hardware of the exemplary computer of FIG. 16.

FIG. 17 illustrates a block diagram of the internal hardware of the computer of FIG. 16. A bus 256 serves as the main information highway interconnecting the other components of the computer. CPU 258 is the central processing unit of the system, performing calculations and logic operations required to execute a program. Read only memory (ROM) 260 and random access memory (RAM) 262 constitute the main memory of the computer.

A disk controller 264 interfaces one or more disk drives to the system bus 256. These disk drives may be external or internal floppy disk drives such as 270, external or internal CD-ROM, CD-R, CD-RW or DVD drives such as 266, or external or internal hard drives 268 or other many devices. As indicated previously, these various disk drives and disk controllers are optional devices.

Program instructions may be stored in the ROM 260 and/or the RAM 262. Optionally, program instructions may be stored on a computer readable carrier such as a floppy disk or a digital disk or other recording medium, a communications signal, or a carrier wave.

Returning to FIG. 17, a display interface 272 permits information from the bus 256 to be displayed on the display 248 in audio, graphic or alphanumeric format. Communication with external devices may optionally occur using various communication ports such as 274.

In addition to the standard components of the computer, the computer also includes an interface 254 which allows for data input through the keyboard 250 or other input device and/or the directional or pointing device 252 such as a remote control, pointer, mouse or joystick.

The many features and advantages of the invention are apparent from the detailed specification. Thus, the appended claims are intended to cover all such features and advantages of the invention which fall within the true spirits and scope of the invention. Further, since numerous modifications and variations will readily occur to those skilled in the art, it is not desired to limit the invention to the exact construction and operation illustrated and described. Accordingly, all appropriate modifications and equivalents may be included within the scope of the invention.

The invention claimed is:

1. A process for the development of scalable, high-performance materials, comprising a computer-assisted knowledge cycle that uses at least one of (i) input from existing experimental data; (ii) correlations generated from at least one of experimental, theoretical, and/or modeling findings; and (iii) theoretical and modeling investigations to generate working hypotheses and suggested steps for at least one of experimental investigations and theoretical investigations to guide the search for better materials.

2. The process of claim 1 in which the knowledge cycle further comprises the use of kinetic modeling to guide catalyst development.

3. The process of claim 1 in which the knowledge cycle further comprises the use of machine learning methods to guide catalyst development.

4. The process of claim 1 in which the knowledge cycle further comprises using kinetic Monte-Carlo simulation to screen catalytic surfaces for catalytic performance.

5. The process of claim 1 in which the knowledge cycle further comprises:

specifying a reactant set, the reactant set comprising a plurality of chemical substances, each of which may engage in a chemical reaction with one or more other substances in the reactant set;

specifying a plurality of possible products that may result from the reaction of two or more of the substances included in the reactant set;

identifying a reaction mechanism set, the reaction mechanism set comprising a plurality of reaction mechanisms, wherein each reaction mechanism comprises a combination of two or more elementary steps representing the chemical process;

selecting a plurality of catalytic materials, each catalytic material being associated with at least one of the reaction mechanisms in the reaction mechanism set, each catalytic material being further associated with experimental data;

associating a kinetic constant value with each elementary step of each reaction mechanism;

generating a kinetic model associated with each reaction mechanism and each catalytic material; and screening, via a processing device, the reaction mechanism set by applying a goodness of fit test to the experimental data associated with each catalyst, eliminating the reaction mechanisms having a worst fit, and grouping the remaining reaction mechanisms associated with each catalytic material to provide a first reaction mechanism subset for each catalytic material.

6. The process of claim 5, further comprising the steps of:

selecting a performance variable; and for the reaction mechanisms contained in the first reaction mechanism subset, identifying one or more associated kinetic parameters to which the performance variable is most sensitive.

7. The process of claim 5, further comprising the steps of:

calculating, using a processing device, a modeled kinetic constant for a plurality of the elementary steps associated with a plurality of the reaction mechanisms;

screening, via the processing device, the first reaction mechanism subset by eliminating the reaction mechanisms having associated kinetic constants that least closely relate to their corresponding modeled kinetic constants; and associating the remaining reaction mechanisms not eliminated in the second screening step with a second reaction mechanism subset.

8. The process of claim 7, wherein the calculating step comprises using molecular modeling investigation to calculate the modeled kinetic constant.

9. The process of claim 7, further comprising the steps of:

selecting a performance variable; and for the reaction mechanisms contained in the second reaction mechanism subset, identifying one or more associated kinetic parameters to which the performance variable is most sensitive.

10. The process of claim 1 in which the knowledge cycle further comprises:

selecting a data set for a set of materials, the data set comprising one or more dependent performance variables for a chemical process and independent variables including, but not limited to, calculated or measured properties of the materials or preparation parameters relating to the materials;

building a model that correlates the dependent performance variables with one or more of the independent variables;

identifying one or more of the independent variables having values that yield improved values of the dependent performance variables based on the results of the model built in the building step;

generating a next step for one of experimental and theoretical investigations aimed at measuring or calculating the dependent variable associated with the improved values of the independent variables; and identifying from one of experimental and theoretical investigations one or more new materials that are associated with the values of the one or more independent variables that yield improved values of the dependent variables.

11. The process of claim 10 wherein the step of building a model comprises the use of recursive partitioning.

12. The process of claim 10 in which one or more dependent performance variables or one or more independent variables are kinetic parameters that have been associated with reaction mechanisms in a reaction mechanism set.

13. The process of claim 10, further comprising the steps of:

applying a Monte Carlo kinetic simulation to calculate at least one modeled performance parameter for each material included in the material set; and selecting at least one materials class based on the results of the Monte Carlo simulation.

14. The process of claim 10 further comprising the steps of:
  selecting a reaction mechanism from a reaction mechanism set, wherein each reaction mechanism in the set comprises a combination of two or more elementary steps in a chemical process;
  applying a Monte Carlo kinetic simulation to calculate at least one modeled performance parameter for each material identified in the identifying step, wherein the simulation is associated with the selected reaction mechanism; and
  selecting at least one materials class based on the results of the Monte Carlo simulation.

15. The process of claim 14 wherein each reaction mechanism in the reaction mechanism set has been screened, using a goodness of fit test, to eliminate reaction mechanisms for which experimental data associated with reaction mechanism catalysts has been determined to have a poor fit.

16. The process of claim 15 wherein each reaction mechanism in the reaction mechanism set has been further screened to eliminate reaction mechanisms having associated kinetic catalysts that least closely relate to corresponding modeled kinetic constants.

17. The process of claim 7, further comprising the steps of:
  selecting a performance variable; and
  for the reaction mechanisms contained in the first reaction mechanism subset, identifying one or more associated kinetic parameters to which the performance variable is most sensitive.

18. A computer-assisted method for the development of scalable, high-performance materials, comprising:
  receiving, by a computer, at least one of the following:
    input from existing experimental data,
    correlations generated from at least one of experimental, theoretical, and/or modeling findings, and
    theoretical and modeling investigations;
  generating, using the computer, one or more working hypotheses and suggested steps for at least one of experimental investigations and theoretical investigations; and
  identifying one or more materials for use in a chemical process.

* * * * *